US012745781B2

(12) United States Patent
Masri et al.

(10) Patent No.: US 12,745,781 B2
(45) Date of Patent: Sep. 29, 2026

(54) CIRCULAR USE OF FOOD RESIDUES BY MICROBIAL FERMENTATION

(71) Applicant: TECHNISCHE UNIVERSITÄT MÜNCHEN, Munich (DE)

(72) Inventors: Mahmoud Masri, Dachau (DE); Thomas Brück, Eichenried (DE); Petra Graban, Geretsried (DE); Farah Qoura, Munich (DE); Corinna Dawid, Freising (DE); Ludovic Gerboin, Moosinning (DE); Melania Pilz, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 226 days.

(21) Appl. No.: 18/703,056

(22) PCT Filed: Oct. 20, 2022

(86) PCT No.: PCT/EP2022/079246
§ 371 (c)(1),
(2) Date: Apr. 19, 2024

(87) PCT Pub. No.: WO2023/067081
PCT Pub. Date: Apr. 27, 2023

(65) Prior Publication Data

US 2024/0415139 A1 Dec. 19, 2024

(30) Foreign Application Priority Data

Oct. 22, 2021 (EP) .................................... 21204299

(51) Int. Cl.
*A23D 7/02* (2006.01)
*A21D 2/16* (2006.01)
(Continued)

(52) U.S. Cl.
CPC ............... *A23D 7/02* (2013.01); *A21D 2/165* (2013.01); *A23G 1/36* (2013.01); *A23J 1/008* (2013.01);
(Continued)

(58) Field of Classification Search
CPC ........... A23D 7/02; A23L 27/24; A21D 2/165; A23G 1/36; A23J 1/008; C12P 7/64; C12P 21/00
(Continued)

(56) References Cited

U.S. PATENT DOCUMENTS

2006/0089283 A1 * 4/2006 Glad ........................ C12N 9/88
435/232

FOREIGN PATENT DOCUMENTS

| | | | |
|---|---|---|---|
| EP | 3696273 | A1 | 8/2020 |
| JP | H06116583 | A | 4/1994 |

OTHER PUBLICATIONS

Gao et al., A novel variable pH control strategy for enhancing lipid production from food waste: Biodiesel versus docosahexaenoic acid; Energy Conversion and Management, vol. 189, Jun. 1, 2019, pp. 60-66 (Year: 2019).*

(Continued)

*Primary Examiner* — Brent T O'Hern
(74) *Attorney, Agent, or Firm* — SALIWANCHIK, LLOYD & EISENSCHENK

(57) ABSTRACT

The present invention relates to a method for producing microbial lipids, optionally for producing microbial lipids and protein biomass and/or aromatic compounds. The present invention further relates to a use of a microbial lipid. The present invention also relates to a composition comprising at least five enzymes.

19 Claims, 5 Drawing Sheets

(51) Int. Cl.
*A23G 1/36* (2006.01)
*A23J 1/00* (2006.01)
*A23L 27/24* (2016.01)
*C12P 7/64* (2022.01)
*C12P 21/00* (2006.01)

(52) U.S. Cl.
CPC ................ *A23L 27/24* (2016.08); *C12P 7/64* (2013.01); *C12P 21/00* (2013.01)

(58) Field of Classification Search
USPC ........................................................... 426/18
See application file for complete search history.

(56) References Cited

OTHER PUBLICATIONS

Ma et al., An integrated engineering system for maximizing bioenergy production from food waste; Applied Energy vol. 206, Nov. 15, 2017, pp. 83-89 (Year: 2017).*

Barros, Rodrigo R. O. et al. "Production of Cellulolytic Enzymes by Fungi Acrophialophora nainiana and Ceratocystis paradoxa Using Different Carbon Sources." Appl Biochem Biotechnol, 161 pp. 448-454, May 1, 2010.

Carmona-Cabello, Miguel et al. "Biodiesel production using microbial lipids derived from food waste discarded by catering services." Bioresource Technology, 323 pp. 1-9, Dec. 24, 2020.

Gao, Zhen et al. " A novel variable pH control strategy for enhancing lipid production from food waste: Biodiesel versus docosahexaenoic acid." Energy Conversion and Management, 189 pp. 60-66, (Year: 2019).

Ma, Yingqun et al. "An integrated engineering system for maximizing bioenergy production from food waste." Applied Energy, 206 pp. 83-89, Nov. 15, 2017.

* cited by examiner

CIRCULAR USE OF FOOD RESIDUES BY MICROBIAL FERMENTATION

CROSS REFERENCE TO RELATED APPLICATIONS

This application is a National Stage Application of International Application Number PCT/EP2022/079246, filed Oct. 20, 2022; which claims priority to European Patent Application No. 21204299.8, filed Oct. 22, 2021; both of which are incorporated herein by reference in their entirety.

FIELD OF THE INVENTION

The present invention relates to a method for producing microbial lipids, optionally for producing microbial lipids and protein biomass and/or aroma compounds. The present invention further relates to a use of a microbial lipid. The present invention also relates to a composition comprising at least five enzymes.

BACKGROUND OF THE INVENTION

Edible oils and fats are known to be essential nutritional requirements for humans. A healthy adult needs approximately 5 g daily of linolenic and unsaturated fatty acids, which cannot be manufactured within the body. In 2018, the global production of edible oil had reached 204 million tons. Palm oil for example accounted for 36% of the total oil produced and its consumption has reached approximately 69 million tons. According to the Food and Agriculture Organization (FAO), the demand for palm oil is anticipated to hit 156 million tons by 2050. In view of a potentially negative impact of plant-based production of triglyceride oils due to excessive land use, monocultures and clearing of biologically diverse habitats in favour of single species, such increasing demand for food such as palm oil is an environmental risk.

Particularly, the growth of the world population results in an inevitable increase in the demand for food, such as edible fats. Furthermore, such increasing demand for food has been associated with an increasing amount of waste per capita and environmental impacts. The Food and Agriculture Organization of the United Nations has estimated that, on average, about one-third of the food produced globally for human consumption is lost or wasted.

According to a WWF study, bakery residues are one of the most discarded foods. In 2015, approximately 4.5 million tons of German bakery products resulted in 1.7 million tons residues. Therefore, 398000 hectare farmland was unnecessarily used and 2.46 million tons greenhouse gases were produced.

Thus, there is the need to reduce food residue(s), e.g. food waste. There is also the need to provide methods for producing foodstuff and raw materials for food in a way that is environmental-friendly. Furthermore, there is a need for means facilitating a sustainable food value chain.

SUMMARY OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the present invention relates to a method for producing microbial lipids, optionally for producing microbial lipids and protein biomass and/or aroma compounds, said method comprising the steps:

a) providing a first substrate, wherein said first substrate is a food residue(s), preferably a food-grade food residue(s);

b) cultivating a first microorganism selected from filamentous fungi and bacteria with said first substrate, and thereby allowing said first microorganism to produce at least one enzyme and an enzymatically treated first substrate, optionally to further produce protein biomass and/or aroma compounds; optionally co-cultivating one or more microalgae with said first microorganism, and thereby allowing said one or more microalgae to produce protein biomass, microbial lipids, and/or aroma compounds;

c) optionally, obtaining said at least one enzyme and pretreating a second substrate with said at least one enzyme, and thereby providing an enzymatically treated second substrate; wherein said second substrate is a food residue(s), preferably a food-grade food residue(s); wherein, preferably, the first substrate and the second substrate are of the same type;

d) cultivating a second microorganism, wherein said second microorganism is an oleaginous microorganism, with a medium comprising said enzymatically treated first substrate and/or, if step c) is present, with a medium comprising said enzymatically treated second substrate, and thereby allowing said oleaginous microorganism to produce microbial lipids;

e) optionally, performing a purely enzymatic treatment of said cultivated second microorganism without any solvent-based extraction or chemicals-based demulsification, to make said microbial lipids produced in step d) amenable for subsequent harvesting; and f) harvesting said microbial lipids produced in step d), preferably by a density-based separation method.

In one embodiment, said food residue(s), at each occurrence, is independently selected from food residue(s) comprising or consisting of bakery food residue(s), e.g. bread, bread rolls, biscuit, muffins, cookies, or cake; fruit food residue(s), e.g. fruit pulp, fruit peel, or fruit juice; vegetable food residue(s), e.g. vegetable peel, vegetable pulp, or vegetable juice; milling food residue(s), e.g. bran or bran flour; fish food residue(s), e.g. fish processing residue; sea food residue(s), e.g. sea food processing residue; brewer's spent grain; cereal food residue(s), e.g. rice, wheat, millet, or maize; restaurant food residue(s), e.g. restaurant leftovers; animal product food residue(s), e.g. milk or cheese; supermarket food residue(s), e.g. food with expired expiration date; or any combination thereof; preferably comprising or consisting of bakery food residue(s), more preferably bread food residue(s).

In one embodiment, said filamentous fungi are selected from *Ceratocystis* sp., e.g. *Ceratocystis fimbriata, Ceratocystis moniliformis*, and *Ceratocystis paradoxa*, preferably *Ceratocystis paradoxa; Trichoderma* sp., e.g. *Trichoderma*

*reesei* and *Trichoderma harzianum; Aspergillus* sp., e.g. *Aspergillus oryzae, Aspergillus tubingensis, Aspergillus terreus*, and *Aspergillus niger; Neurospora* sp., e.g. *Neurospora intermedia; Monascus* sp., e.g. *Monascus purpureus; Rhizopus* sp., e.g. *Rhizopus oryzae; Fusarium* sp., e.g. *Fusarium venenatum; Thermomyces* sp.; *Penicillium* sp.; *Aureobasillium* sp.; *Ischnoderma* sp., e.g. *Ischnoderma benzoinum; Polyporus* sp., e.g. *Polyporus durus; Pycnoporus* sp., e.g. *Pycnoporus cinnabarinus; Phanerochaete* sp., e.g. *Phanerochaete chrysosporium*; and *Xylaria* sp; preferably selected from *Ceratocystis* sp., *Trichoderma* sp., *Aspergillus* sp., and *Fusarium* sp;

said bacteria are selected from *Clostridium* sp., e.g. *Clostridium stercorarium, Clostridium beijerinckii*, and *Clostridium acetobutylicum; Halobacillus* sp., e.g. *Halobacillus trueperi* and *Halobacillus karajensis; Halomonas* sp., e.g. *Halomonas meridiana* and *Halomonas elongata; Rhodothermus* sp., e.g. *Rhodothermus marinus; Streptomyces* sp., e.g. *Streptomyces griseus, Streptomyces olivochromogenes, Streptomyces griseorubens*, and *Streptomyces matensis*; and *Bacillus* sp., e.g. *Bacillus nato, Bacillus subtilis, Bacillus licheniformis*, and *Bacillus stearothermophilus*; and/or said microalgae are selected from *Chlorella* sp., e.g. *Chlorella vulgaris* and *Chlorella* protothecoides; *Scenedesmus* sp., e.g. *Scenedesmus obliquus; Dunaliella* sp., e.g. *Dunaliella salina; Haematococcus* sp., e.g. *Haematococcus pluvialis; Crypthecodinium* sp., e.g. *Crypthecodinium cohnii; Schizochytrium* sp., e.g. *Schizochytrium limacinum*; and *Tetraselmis* sp., e.g. *Tetraselmis chui*; preferably selected from *Chlorella* sp. and *Scenedesmus* sp.

In one embodiment, said second microorganism is an oleaginous microorganism selected from oleaginous yeasts, oleaginous fungi, oleaginous bacteria, and oleaginous microalgae; wherein, preferably, said oleaginous yeasts are selected from *Cutaneotrichosporon* sp., e.g. *Cutaneotrichosporon oleaginosus; Trichosporon* sp., e.g. *Trichosporon oleaginosus, Trichosporon capitatu*, and *Trichosporon asahii; Rhodospirillum* sp.; *Rhodosporidium* sp., e.g. *Rhodosporidium toruloides; Rhodosporon* sp.; *Candida* sp., e.g. *Candida viswanathii* and *Candida freyschussii; Cryptococcus* sp., e.g. *Cryptococcus curvatus; Lipomyces* sp., e.g. *Lipomyces starkeyi; Yarrowia* sp., e.g. *Yarrowia lipolytica; Rhodotorula* sp., e.g. *Rhodotorula graminis, Rhodotorula gracilis*, and *Rhodotorula glutinis*; and *Apiotrichum* sp., e.g. *Apiotrichum curvarum*; preferably *Cutaneotrichosporon* sp., more preferably *Cutaneotrichosporon oleaginosus;* said oleaginous fungi are selected from *Cunninghamella* sp., e.g. *Cunninghamella echinulate; Aspergillus* sp., e.g. *Aspergillus oryzae, Aspergillus tubingensis, Aspergillus terreus*, and *Aspergillus niger; Neurospora* sp., e.g. *Neurospora intermedia; Monascus* sp., e.g. *Monascus purpureus; Rhizopus* sp., e.g. *Rhizopus oryzae; Fusarium* sp., e.g. *Fusarium venenatum; Mucor* sp., e.g. *Mucor moelleri; Mortierella* sp., e.g. *Mortariella isabellina* and *Mortierella alpine*, preferably *Mortierella alpine*; and *Humicola* sp.;

said oleaginous bacteria are selected from *Rhodococcus* sp.; *Acinetobacter* sp.; and *Bacillus* sp.; and said oleaginous microalgae are selected from *Chlorella* sp., *Pseudochlorococcum* sp., *Nannochloris* sp., *Nannochloropsis* sp., *Isochrysis* sp., *Tribonema* sp., *Dunaliella* sp., *Ankistrodesmus* sp., *Botryococcus* sp., *Pavlova* sp., *Scenedesmus* sp., *Skeletonema* sp., and *Nitzschia* sp.;

wherein, more preferably, said second microorganism is an oleaginous yeast selected from *Cutaneotrichosporon* sp., e.g. *Cutaneotrichosporon oleaginosus.*

In one embodiment, said second microorganism is an oleaginous yeast selected from *Cutaneotrichosporon oleaginosus, Trichosporon oleaginosus, Trichosporon capitatu, Trichosporon asahii, Lipomyces starkeyi, Rhodosporidium toruloides, Yarrowia lipolytica, Rhodotorula graminis, Rhodotorula gracilis, Rhodotorula glutinis, Apiotrichum curvarum, Cryptococcus curvatus, Candida viswanathii*, and *Candida freyschussii*; preferably *Cutaneotrichosporon oleaginosus.*

In one embodiment, said step b) of said method comprises cultivating a first microorganism selected from filamentous fungi and bacteria with said first substrate, and thereby allowing said first microorganism to produce at least one enzyme, an enzymatically treated first substrate, and protein biomass and/or aroma compounds; optionally further comprises co-cultivating one or more microalgae with said first microorganism, and thereby allowing said one or more microalgae to produce protein biomass, microbial lipids, and/or aroma compounds.

In one embodiment, said method further comprises a step of harvesting said protein biomass and/or said aroma compounds, preferably using any of centrifugation, filtration, organophilic pervaporation, solid-phase micro extraction, distillation, and combinations thereof.

In one embodiment, said medium further comprises an additional carbon source, nitrogen source, trace metal, and/or vitamin.

In one embodiment, said method further comprises a step of pretreating said first substrate and/or, if step c) is present, pretreating said second substrate, by mechanical pretreatment, preferably by milling, mixing, shredding, and/or sieving said substrate(s);

dissolving said substrate(s) in a dissolvent, preferably in water;

chemical hydrolysis of said substrate(s), preferably using an acid, e.g. sulfuric acid;

thermal pretreatment of said substrate(s), preferably at a temperature of from 50° C. to 200° C. for 10 min to 240 min, more preferably at a temperature of from 80° C. to 170° C. for 30 min to 90 min;

fermentative pretreatment of said substrate(s), preferably an anaerobic fermentation; and/or enzymatic pretreatment of said substrate(s) using one or more enzymes, optionally commercially available enzymes;

wherein said one or more enzymes are selected from proteases, e.g. endo- and exo-peptidases, serine endopeptidase, subtilisin A, and pepsin; and hydrolases, preferably glycoside hydrolases, more preferably glycoside hydrolases selected from α-amylases, amyloglucosidases, cellulases, hemicellulases, xylanases, xyloglucase, galactanase, arabinase, mannanase, lipase, glucoamylases, and pectinases.

In one embodiment, said method comprises said step e) of performing said purely enzymatic treatment of said cultivated second microorganism without any solvent-based extraction or chemicals-based demulsification, wherein said purely enzymatic treatment of said cultivated second microorganism is a treatment of said microorganism with a hydrolase, alone, or in combination with/followed by a protease.

In one embodiment, said method comprises step c) of obtaining said at least one enzyme and pretreating said second substrate with said at least one enzyme, wherein said pretreating comprises contacting said second substrate with said at least one enzyme in the form of a liquid enzyme preparation obtained, preferably directly obtained, from culturing said first microorganism, or in the form of a freeze-dried enzyme preparation, optionally a freeze-dried enzyme preparation reconstituted in solution.

In one embodiment, said at least one enzyme contains one or several activities selected from enzyme activities of cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; and laminarinase; optionally selected from enzyme activities of cellulase; lichenase; xylanase; arabinanase; amylase, e.g. α-amylase; limit dextrinase; pullulanase; protease; galactanase; mannanase; rhamnogalacturonan hydrolase; and rhamnogalacturonan lyase.

In one embodiment, said method is a method of producing microbial lipids and preparing foodstuff therefrom, wherein said method further comprises a step g) of preparing a foodstuff comprising the microbial lipid harvested in step f), preferably a bakery product, e.g. bread, bread roll, biscuit, muffin, cookie, or cake; a confectionery product, e.g. flour confectionary or sugar confectionary; a dairy product, e.g. ice cream or baby milk; a spread, e.g. margarine, mayonnaise, or soft cheese; a convenience food, e.g. instant noodles, pizza, pizza dough, or sauce; a beverage; vegetarian or vegan food, e.g. meat analogues and milk analogues; sweets, e.g. cocoa-free chocolate; and/or a chocolate product;

wherein, optionally, said method further comprises a step h) of recycling a food residue(s) of said foodstuff by using said food residue(s) of said foodstuff as said first substrate and/or, if step c) is present, as said second substrate.

In a further aspect, the present invention relates to a use of a microbial lipid, preferably a microbial lipid produced using a method as defined above, in the production of a foodstuff, preferably a bakery product, e.g. bread, bread roll, biscuit, muffin, cookie, or cake; a confectionery product, e.g. flour confectionary or sugar confectionary; a dairy product, e.g. ice cream or baby milk; a spread, e.g. margarine, mayonnaise, or soft cheese; a convenience food, e.g. instant noodles, pizza, pizza dough, or sauce; a beverage; vegetarian or vegan food, e.g. meat analogues and milk analogues; sweets, e.g. cocoa-free chocolate; and/or a chocolate product.

In a further aspect, the present invention relates to a composition, preferably a composition produced in step b) of the method as defined above, comprising at least five, preferably at least six, more preferably at least seven enzymes selected from cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; and laminarinase;

wherein, optionally, said composition comprises cellulase; amylase; hemicellulase; limit dextrinase e.g. malt limit dextrinase; and pectinase; or cellulase; lichenase; xylanase; arabinanase; amylase, e.g. α-amylase; limit dextrinase; pullulanase; protease; galactanase; and mannanase; or cellulase; xylanase; arabinanase; amylase, e.g. α-amylase; limit dextrinase; pullulanase; galactanase; mannanase; rhamnogalacturonan hydrolase; and rhamnogalacturonan lyase.

In a further aspect, the present invention relates to a method for producing microbial lipids and protein biomass and/or aroma compounds, wherein said method comprises a method for producing microbial lipids, as defined above, wherein, in step b), said first microorganism further produces protein biomass and/or aroma compounds, and/or, if step b) comprises co-cultivating one or more microalgae with said first microorganism, said microalgae produce protein biomass and/or aroma compounds.

In one embodiment, in step d), said second microorganism produces microbial lipids, and further produces protein biomass and/or aroma compounds.

In one embodiment, said method comprises a step of harvesting said protein biomass and/or aroma compounds.

In one embodiment, said method for producing microbial lipids, said microbial lipids, said protein biomass, said aroma compounds, said first microorganism, said co-cultivating, said microalgae, said second microorganism, and said harvesting are as defined above.

In a further aspect, the present invention relates to a method of preparing foodstuff, comprising a) providing microbial lipids using a method for producing microbial lipids, as defined above; optionally further providing protein biomass and/or aroma compounds, preferably using a method for producing microbial lipids and protein biomass and/or aroma compounds, as defined above;

b) preparing foodstuff comprising said microbial lipids, optionally further comprising said protein biomass and/or aroma compounds.

In one embodiment, said foodstuff, said microbial lipids, said method for producing microbial lipids, said protein biomass, said aroma compounds, and said method for producing microbial lipids and protein biomass and/or aroma compounds, are as defined above.

DETAILED DESCRIPTION

It is an aim of the invention to provide a method for sustainable production of foodstuff, such as microbial lipids and protein biomass and/or aroma compounds. In one embodiment, such microbial lipids and protein biomass can be directly consumed by a human or an animal, or can be incorporated into food products such as bakery products. Furthermore, it is an aim of the invention to reduce food waste, e.g. by using food residues to prepare value of the products, such as microbial lipids and protein biomass and/or aroma compounds. In particular, it is an aim of the invention to recycle food residues into the food value chain. Such recycling of food residues allows to provide a sustainable food value chain.

The method of the invention is advantageous in that the food value chain is converted from a linear value chain, with food residues and/or food loss, to a circular value chain which recycles food residues as substrates for the production of valuable products, such as microbial oil, protein biomass, and/or aroma compounds. The method of the invention improves the efficiency of resource use, e.g. the use of food raw materials. Furthermore, the method of the invention allows for a valorization of food residues. The economic, environmental, and social costs of food waste are thus successfully reduced by a method of the invention.

The term "microbial lipids", as used herein, relates to lipids produced by oleaginous microorganisms, e.g. yeast oil, bacterial oil, and/or fungal oil. In one embodiment, the term "microbial lipid" is used interchangeably with "single cell oil" or "microbial oil". Typically, microbial lipids are rich in unsaturated fatty acids. In one embodiment, the microbial lipids are edible microbial lipids. Such microbial lipids can be used to prepare foodstuff comprising the microbial lipids. For example, microbial lipids can be used to replace fats with high saturated fatty acid content and/or fats that are environmentally unfriendly such as palm oil. Microbial lipids have fatty acid compositions similar to those of vegetable oils but they are considered more sustainable. In fact, the production of microbial lipids is unaffected by seasons, they can be produced in large quantities and with reduced space requirements, and they can be produced from a wide range of carbon sources by oleaginous microorganisms. Microorganisms are defined oleaginous as a result of their ability to accumulate lipids, e.g. by as much as 20% of their dry cellular weight (DCW). For example, oleaginous microorganisms include several eukaryotic microorganisms such fungi, yeasts, algae and some species of bacteria able to accumulate lipids in the form of triglycerides (TAGs) and free fatty acids (FA). In one embodiment, the composition of the microbial lipid produced with a method of the invention can be customized by the skilled person by selecting appropriate microorganisms and/or substrates.

In one embodiment, the term "protein biomass", as used herein, relates to biomass with a high protein content, e.g. a protein content of up to 60 wt % or more of the dry biomass. In one embodiment, the protein biomass has a protein content of at least 20 wt % or at least 50 wt %, preferably at least 60 wt % or at least 80 wt %, more preferably at least 90 wt % or at least 95 wt %, even more preferably at least 99 wt %, and/or consisting of protein. In one embodiment, the protein biomass comprises or consists of mycoprotein. In one embodiment, protein biomass, e.g. comprising or consisting of mycoprotein, is produced as a side product of a method for producing microbial lipids of the invention. In one embodiment, the protein biomass comprises or consists of mycoprotein, e.g. mycoprotein produced by *Fusarium venenatum, Neurospora intermedia*, and/or *Aspergillus oryzae*. In one embodiment, the protein biomass is edible protein biomass. For example, such protein biomass can be used to prepare foodstuff comprising said protein biomass. Moreover, microbial protein biomass can be further processed into protein-rich feed and food supplements. In one embodiment, said protein biomass is enzymatically hydrolyzed or is directly used for further processing, e.g. processing into a foodstuff. In one embodiment, protein biomass comprises protein(s) selected from cell wall proteins, structural proteins, and membrane proteins. In one embodiment, the protein biomass, e.g. produced as a side product of a method for producing microbial lipids of the invention, comprises mycoprotein, e.g. mycoprotein produced by *Fusarium venenatum, Neurospora intermedia*, and/or *Aspergillus oryzae*. In one embodiment, the first microorganism comprises *Fusarium venenatum, Neurospora intermedia*, and/or *Aspergillus oryzae*. In one embodiment, the first microorganism does not comprise or consist of *Aspergillus oryzae*. In one embodiment, the protein biomass is produced by *Fusarium venenatum, Neurospora intermedia*, and/or *Aspergillus oryzae*. In one embodiment, the protein biomass, preferably protein biomass produced by *F. venenatum*, comprises an amino acid content: alanine in the range of from 4 to 6.5 wt %, e.g. about 5.25 wt %; arginine in the range of from 5.5 to 6.5 wt %, e.g. about 6.13 wt %; aspartic acid in the range of from 5.0 to 6.0 wt %, e.g. about 5.75 wt %; cystine in the range of from 2.0 to 4.5 wt %, e.g. about 3.25 wt %; glutamic acid in the range of from 12.0 to 14 wt %, e.g. about 13.13 wt %; glycine in the range of from 3.5 to 5.5 wt %, e.g. about 4.75 wt %; histidine in the range of from 2.0 to 4 wt %, e.g. about 3.00 wt %; isoleucine in the range of from 3.5 to 5.5 wt %, e.g. about 4.25 wt %; leucine in the range of from 2.0 to 3.5 wt %, e.g. about 2.75 wt %; lysine in the range of from 6.0 to 8.5 wt %, e.g. about 7.25 wt %; methionine in the range of from 2.0 to 4.0 wt %, e.g. about 3.00 wt %; phenylalanine in the range of from 3.0 to 6.0 wt %, e.g. about 4.50 wt %; proline in the range of from 1.5 to 3.5 wt %, e.g. about 2.25 wt %; serine in the range of from 5.0 to 6.5 wt %, e.g. about 5.75 wt %; threonine in the range of from 2.5 to 4.5 wt %, e.g. about 3.50 wt %; tyrosine in the range of from 3.0 to 6.0 wt %, e.g. about 4.50 wt %; and/or valine in the range of from 4.0 to 6.0 wt %, e.g. about 5.00 wt %. In one embodiment, said protein biomass produced in step b) comprises or consists of

| | | |
|---|---|---|
| a) | Protein (g) | 11.5 |
| | Total carbohydrate (g) | 1.7 |
| | Total fat (g) | 2.9 |
| | Dietary fibre (NSP) (g) | 6.0 |
| | Salt (mg) | 4, |
| | e.g. a biomass produced by *Fusarium venenatum*; | |
| b) | Protein: | 91 wt % |
| | Lipid | 2 wt % |
| | Glucans | 1 wt %, |
| | e.g. a biomass produced by *Trichoderma reesei*; or | |
| c) | Protein: | 23.1 wt % |
| | Lipid | 19 wt % |
| | Chitin | 20 wt % |
| | Glucans | 35 wt % |
| | e.g. a biomass produced by *Aspergillus niger*. | |

In one embodiment, in step b), the first microorganism produces protein biomass and/or the first microorganism is co-cultivated with one or more microalgae that produces protein biomass. In one embodiment, the method comprises a step of obtaining protein biomass produced in step b), e.g. by any of centrifugation, filtration, sedimentation, coagulation, floating, and combinations thereof, preferably by centrifugation, filtration, and combinations thereof. In one embodiment, in step d), the second microorganism further produces protein biomass, as a coproduct of the production of microbial lipids. In one embodiment, the method comprises a step of obtaining protein biomass produced in step d), e.g. by any of centrifugation, filtration, sedimentation, coagulation, floating, and combinations thereof, preferably by centrifugation, filtration, and combinations thereof. In one embodiment, the terms "harvesting protein biomass" and "obtaining protein biomass" are used interchangeably. In one embodiment, said method is a method of producing microbial lipids and preparing foodstuff therewith, wherein said preparing foodstuff further comprises incorporating said protein biomass into said foodstuff. In one embodiment, a method of the invention is a method for producing microbial lipids and protein biomass, the first microorganism is preferably a microorganism which produces at least 30% of its biomass as protein.

Advantageously, the method of the invention allows to produce microbial protein biomass as a side product of a method of producing microbial lipids. Thus, an alternative to the intensive farming of livestock to produce protein is the cultivation of microorganisms to produce edible microbial protein biomass. In one embodiment, the protein biomass produced with a method of the invention can be consumed directly as biomass, or as a supplement to increase the protein content of foodstuff. An advantage of the method of the invention is that the production of protein biomass is economically viable and thus can successfully compete with more established meat alternatives, such as tofu and other soy derivatives, as well as meat itself. A further advantage is that the first and second microorganism of the invention can be cultivated in a large-scale cultivation and provide high quantities of microbial lipids and protein biomass and/or aroma compounds.

In one embodiment, the term “aroma compounds”, as used herein, relates to a chemical compound that has a smell or odor, preferably a pleasant smell or odor, e.g. an odorant, aroma, fragrance or flavor. In one embodiment, an aroma compound is a flavor compound. In one embodiment, an aroma compound is produced as a side product of the method of the invention. In one embodiment, an aroma compound is selected from benzaldehyde, eugenol, cinnamaldehyde, ethyl maltol, vanillin, anisole, anethole, estragole, thymol, geranyl acetate, methyl formate, methyl acetate, methyl propionate, methyl butyrate, ethyl acetate, ethyl butyrate, propyl acetate, isobutyl acetate, isoamyl acetate, pentyl butyrate, pentyl pentanoate, octyl acetate, benzyl acetate, methyl anthranilate, hexyl acetate, myrcene, geraniol, nerol, citral, citronellal, citronellol, linalool, nerolidol, ocimene, limonene, camphor, menthol, carvone, terpineol, alpha-ionone, thujone, eucalyptol, jasmone, ethyl caproate, isoamyl alcohol, 3-methyl-1-butanol, 1-octen-3-ol, and combinations thereof; preferably selected from citronellol, geraniol, ethyl acetate, propyl acetate, isobutyl acetate, isoamyl acetate, and combinations thereof. In one embodiment, the aroma compound is ethyl acetate, wherein the aroma compound is produced by a filamentous fungus selected from *Ceratocystis* sp., e.g. *Ceratocystis fimbriata*, e.g. with a substrate being coffee husk. In one embodiment, the aroma compound is selected from ethyl caproate, isoamyl alcohol, 3-methyl-1-butanol, 1-octen-3-ol, and/or ethyl acetate, wherein the aroma compound is produced by a filamentous fungus selected from *Neurospora* sp., e.g. with a substrate being rice such as pregelatinized rice.

In one embodiment, the aroma compound is obtained using any of distillation, organophilic pervaporation, solid-phase micro extraction, and combinations thereof. In one embodiment, an aroma compound is secreted into a cultivation medium, and said aroma compound is obtained from said cultivation medium, e.g. by distillation such as distillation under vacuum with supercooling, by organophilic pervaporation, by solid-phase micro extraction, and combinations thereof. Aroma is one of the most important attributes of food and is directly associated with product acceptance by the consumers. The method of the invention allows to produce such aroma compounds in an efficient way as a side product of a method of producing microbial lipids. Advantageously, such biotechnologically produced aroma compounds are sustainable aroma compounds, e.g. useful as additives for the food industry.

The term “first substrate”, as used herein, relates to a food residue(s), preferably comprising nutrients for growth, metabolism, and/or activity of microorganisms such as the first and/or second microorganism, e.g. carbohydrates, proteins, fats, and minerals. In one embodiment, the first substrate is a material which provides substances that allow growth of microorganisms. In one embodiment, the first substrate is selected from food residue(s) comprising or consisting of bakery food residue(s), e.g. bread, bread rolls, biscuit, muffins, cookies, or cake; fruit food residue(s), e.g. fruit pulp, fruit peel, or fruit juice; vegetable food residue(s), e.g. vegetable peel, vegetable pulp, or vegetable juice; milling food residue(s), e.g. bran or bran flour; fish food residue(s), e.g. fish processing residue; sea food residue(s), e.g. sea food processing residue; brewer’s spent grain; cereal food residue(s), e.g. rice, wheat, millet, or maize; restaurant food residue(s), e.g. restaurant leftovers; animal product food residue(s), e.g. milk or cheese; supermarket food residue(s), e.g. food with expired expiration date; or any combination thereof; preferably bakery food residue(s), more preferably bread food residue(s). In one embodiment, the first microorganism produces at least one enzyme in response to the presence of the first substrate. For example, the at least one enzyme is/are adaptive enzyme(s) that are configured to enzymatically act on the components of the substrate. In one embodiment, by contacting the first microorganism with the first substrate, the first microorganism is stimulated to produce enzymes suitable to enzymatically act on components of the substrate, e.g. to digest the substrate and/or to use components of the substrate for growth. In one embodiment, the first substrate is an inducing system for the first microorganism, particularly an inducing system for producing enzymes specific for the substrate. In one embodiment, the first substrate is used to prepare at least one enzyme, preferably an enzyme mix, configured to pretreat a second substrate to provide a growth medium therefrom. In one embodiment, a second substrate is pretreated, e.g. digested, with said at least one enzyme, preferably enzyme mix, to obtain a medium comprising nutrients for the second microorganism. In one embodiment, the enzymatically treated first substrate and/or enzymatically treated second substrate is/are a medium for growing the second microorganism.

In one embodiment, said first substrate is an inducing system for said first microorganism to stimulate said first microorganism to produce enzymes that are tailored to digest the substrate. Such tailored enzyme system is then used to digest the second substrate, which is preferably of the same type as the first substrate. For example, both the first and second substrate are the same type of food residue (s), e.g. bakery food residue(s). In one embodiment, said enzymes obtained from the cultivation of the first microorganism with said inducing system, i.e. the first substrate, are prepared separately and are used as a liquid preparation or as a freeze-dried preparation that is optionally reconstituted in solution for further use.

In one embodiment, the term “food residue(s)”, as used herein, relates to any food substance, raw or cooked, which is discarded, or intended or required to be discarded. The term “residue(s)”, as used herein, includes the singular form “residue” and the plural form “residues”. In many of the embodiments, when using the term “residue(s)” in combination with a verb which is in a singular form, the combination of the verb and the term “residue(s)” is to be understood as relating to both the singular and plural form, even if the verb is in a singular form. Likewise, when using the term “residue(s)” in combination with a verb which is in a plural form, the combination of the verb and the term “residue(s)” is to be understood as relating to both the singular and plural form, even if the verb is in a plural form. Food residue(s) further relates to uneaten food and food preparation residue(s) from residences and commercial establishments such as grocery stores, restaurants, produce stands, institutional cafeterias and kitchens, and industrial sources like employee lunchrooms. For example, food residue(s) is food that is left uneaten or unused, e.g. food residues derived from food manufacturing, food logistics, food storage, food retail, and consumer food residue(s), such as of households, restaurants, and caterings. In one embodiment, food residue(s) is independently selected from food residue(s) comprising or consisting of bakery food residue(s), e.g. bread, bread rolls, biscuit, muffins, cookies, or cake; fruit food residue(s), e.g. fruit pulp, fruit peel, or fruit juice; vegetable food residue(s), e.g. vegetable peel, vegetable pulp, or vegetable juice; milling food residue(s), e.g. bran or bran flour; fish food residue(s), e.g. fish processing residue; sea food residue(s), e.g. sea food processing residue; brewer's spent grain; cereal food residue(s), e.g. rice, wheat, millet, or maize; restaurant food residue(s), e.g. restaurant leftovers; animal product food residue(s), e.g. milk or cheese; supermarket food residue(s), e.g. food with expired expiration date; or any combination thereof; preferably comprising or consisting of bakery food residue(s), more preferably bread food residue(s). In one embodiment, the food residue(s) is food-grade food residue(s). In one embodiment, the food residue(s) is not decomposed and/or rotten food. In one embodiment, the food residue(s) does not comprise inedible mold. In one embodiment, the food residue(s) does not comprise any components toxic and/or harmful to the health of a human and/or an animal. For example, a fruit or vegetable food residue(s) is a residue of a juice preparation, convenience food preparation, and/or canning process, such as a pulp or peel of a fruit or vegetable, e.g. a carrot, pear, apple, potato, banana, or lychee. In one embodiment, said food residue(s) has food-grade. In one embodiment, said food residue(s) does not comprise or consist of meat. In one embodiment, said food residue(s) is without meat. In one embodiment, the term "food residue(s)" comprises food waste and food loss, e.g. food loss along the food supply chain from harvest, e.g. post-harvest loss. In one embodiment, said food residue(s) comprises or consists of food-grade food residue(s), preferably said food residue(s) does not contain chemical contaminants, infectious agents, and/or pathogens. In a preferred embodiment, food residue(s) is bakery product food residue(s), e.g. bread food residue(s). In one embodiment, the terms "bakery food residue(s)" and "bakery product food residue(s)" are used synonymously. In one embodiment, a bakery food residue(s) relates to any food residue(s) occurring at any stage throughout the supply chain, from initial agricultural production to final household consumption. In one embodiment, a food residue(s) used as a first substrate and a food residue(s) used as a second substrate are the same type of food residue(s), e.g. the first substrate and the second substrate are both bakery product food residue(s), e.g. are both bread residues. In one embodiment, the first substrate is an inducing system for the first microorganism to produce said at least one enzyme tailored to degrade said first substrate, preferably said first and second substrate. In one embodiment, said food residue(s) is unspoiled food.

In one embodiment, the term "food-grade food residue(s)", as used herein, relates to material that is safe for consumption, e.g. human consumption and/or animal consumption, and/or is safe for being further processed into consumable food/feed products. For example, such food-grade food residue(s) is food residue(s) which is not spoiled and/or rotten. In one embodiment, food-grade food residue(s) is edible food residue(s). In one embodiment, food-grade food residue(s) is unspoiled food residue(s). In one embodiment, food-grade food residue(s) comprises or consists of edible components. In one embodiment, food-grade food residue(s) does not comprise components toxic for humans and/or animals. In one embodiment, food-grade food residue(s) consists of non-toxic components or consists of components in a non-toxic concentration. In one embodiment, food-grade food residue(s) does not include food waste. In one embodiment, food-grade food residue(s) does not contain chemical contaminants, infectious agents, and/or pathogens. In one embodiment, food-grade food residue(s) does not comprise chemical contaminants and/or pathogens. In one embodiment, said food residue(s), preferably said food-grade food residue(s), does not comprise uncooked food, spoiled food, expired food, and leftovers from plates such as customers' plates. In one embodiment, said food residue(s), preferably said food-grade food residue(s), consists of food. In one embodiment, said food residue(s), preferably said food-grade food residue(s), does not comprise non-food components.

The term "first microorganism", as used herein, relates to a microorganism selected from filamentous fungi and bacteria. In one embodiment, the first microorganism is capable of producing at least one enzyme, preferably an enzyme mix, adapted to the first substrate, e.g. adapted to digest the first substrate. In one embodiment, the first microorganism produces at least one enzyme that can be used to subsequently digest a second substrate to provide a growth medium for a second microorganism, and provides an enzymatically treated substrate, which can be used as a growth medium for the second microorganism. In one embodiment, in step b), the first microorganism produces at least one enzyme, preferably an enzyme mix, which is used in step c) to pretreat a second substrate, thereby providing an enzymatically treated second substrate which can be used as a growth medium for the second microorganism.

In one embodiment, the first microorganism is selected from filamentous fungi and bacteria, wherein filamentous fungi are selected from *Ceratocystis* sp., e.g. *Ceratocystis fimbriata, Ceratocystis moniliformis*, and *Ceratocystis paradoxa*, preferably *Ceratocystis paradoxa; Trichoderma* sp., e.g. *Trichoderma reesei* and *Trichoderma harzianum; Aspergillus* sp., e.g. *Aspergillus oryzae, Aspergillus tubingensis, Aspergillus terreus*, and *Aspergillus niger; Neurospora* sp., e.g. *Neurospora intermedia; Monascus* sp., e.g. *Monascus purpureus; Rhizopus* sp., e.g. *Rhizopus oryzae; Fusarium* sp., e.g. *Fusarium venenatum; Thermomyces* sp.; *Penicillium* sp.; *Aureobasillium* sp.; *Ischnoderma* sp., e.g. *Ischnoderma benzoinum; Polyporus* sp., e.g. *Polyporus durus; Pycnoporus* sp., e.g. *Pycnoporus cinnabarinus; Phanerochaete* sp., e.g. *Phanerochaete chrysosporium*; and *Xylaria* sp; preferably selected from *Ceratocystis* sp., *Trichoderma* sp., *Aspergillus* sp., and *Fusarium* sp; and wherein said bacteria are selected from *Clostridium* sp., e.g. *Clostridium stercorarium, Clostridium beijerinckii*, and *Clostridium acetobutylicum; Halobacillus* sp., e.g. *Halobacillus trueperi* and *Halobacillus karajensis; Halomonas* sp., e.g. *Halomonas meridiana* and *Halomonas elongata; Rhodothermus* sp., e.g. *Rhodothermus marinus; Streptomyces* sp., e.g. *Streptomyces griseus, Streptomyces olivochromogenes, Streptomyces griseorubens*, and *Streptomyces matensis*; and *Bacillus* sp., e.g. *Bacillus nato, Bacillus subtilis, Bacillus licheniformis*, and *Bacillus stearothermophilus*. In one embodiment, the first microorganism is selected from said filamentous fungi and said bacteria, wherein the first microorganism is not *Aspergillus awamori* and/or is not *Aspergillus oryzae*. In one embodiment, the first microorganism is selected from said filamentous fungi and said bacteria, wherein said filamentous fungi do not include *Aspergillus awamori* and/or *Aspergillus oryzae.*

In one embodiment, *Aspergillus* is *Aspergillus niger*, e.g. *Aspergillus niger* van Tiegheim ATCC 10535, or *Aspergillus terreus*, e.g. *Aspergillus terreus* CBS 117.37. In one embodiment, if the first microorganism is an *Aspergillus* sp., the *Aspergillus* sp. is selected from *Aspergillus niger*, e.g. *Aspergillus niger* van Tiegheim ATCC 10535, and *Aspergillus terreus*, e.g. *Aspergillus terreus* CBS 117.37. In one embodiment, *Aspergillus niger* is *Aspergillus niger* van Tieghem. In one embodiment, *Aspergillus niger* is *Aspergillus niger* van Tiegheim ATCC 10535. In one embodiment, *Aspergillus* is not *Aspergillus awamori*. In one embodiment, if the first microorganism is an *Aspergillus* sp., the *Aspergillus* sp. is not *Aspergillus awamori* and/or is not *Aspergillus oryzae*. In one embodiment, the first microorganism is not *Aspergillus awamori* and/or is not *Aspergillus oryzae*.

In one embodiment, *Ceratocystis paradoxa* is *Ceratocystis paradoxa* CBS 374.83 or *Ceratocystis paradoxa* DSM 63054. In one embodiment, said first microorganism is selected from *Aspergillus* sp., preferably *Aspergillus niger*, more preferably *Aspergillus niger* van Tiegheim ATCC 10535; and *Ceratocystis* sp., preferably *Ceratocystis paradoxa*, more preferably *Ceratocystis paradoxa* CBS 374.83. In one embodiment, said *Aspergillus* sp. do not include *Aspergillus awamori* and/or *Aspergillus oryzae*. In one embodiment, the first microorganism is not *Aspergillus awamori*. In one embodiment, the first microorganism is not *Aspergillus oryzae*.

In one embodiment, a first microorganism is an organism capable of producing at least one enzyme, and further capable of producing protein biomass, for example a microorganism selected from *Aspergillus* sp., e.g. *Aspergillus oryzae; Neurospora* sp., e.g. *Neurospora intermedia; Monascus* sp., e.g. *Monascus purpureus; Rhizopus* sp., e.g. *Rhizopus oryzae; Trichoderma* sp.; and *Fusarium* sp., e.g. *Fusarium venenatum*; preferably *Fusarium venenatum*. In one embodiment, said first microorganism is a microorganism producing at least one enzyme and protein biomass, and said microorganism is selected from *Aspergillus* sp., e.g. *Aspergillus oryzae; Neurospora* sp., e.g. *Neurospora intermedia; Monascus* sp., e.g. *Monascus purpureus; Rhizopus* sp., e.g. *Rhizopus oryzae; Trichoderma* sp.; and *Fusarium* sp., e.g. *Fusarium venenatum*; preferably *Fusarium venenatum.*

In one embodiment, a first microorganism is an organism capable of producing at least one enzyme, and further capable of producing an aroma compound, and is selected from *Ceratocystis*, e.g. *Ceratocystis fimbriata, Ceratocystis moniliformis*, and *Ceratocystis paradoxa; Aspergillus* sp., e.g. *Aspergillus oryzae, Aspergillus tubingensis*, and *Aspergillus niger*, preferably *Aspergillus niger; Ischnoderma* sp., e.g. *Ischnoderma benzoinum; Polyporus* sp., e.g. *Polyporus durus; Pycnoporus* sp., e.g. *Pycnoporus cinnabarinus; Phanerochaete* sp., e.g. *Phanerochaete chrysosporium*. In a preferred embodiment, a first microorganism is an organism capable of producing at least one enzyme, and further capable of producing an aroma compound, and is selected from *Aspergillus niger, Ceratocystis* fimbriata, *Ceratocystis* moniliformis, *Ceratocystis paradoxa, Ischnoderma benzoinum, Polyporus durus, Pycnoporus cinnabarinus*, and *Phanerochaete chrysosporium*; preferably is *Ceratocystis paradoxa* or *Aspergillus niger*. In one embodiment, said first microorganism is a microorganism producing at least one enzyme and an aroma compound, and said microorganism is selected from *Ceratocystis* sp., e.g. *Ceratocystis paradoxa*, such as *Ceratocystis paradoxa* CBS 374.83 or *Ceratocystis paradoxa* DSM 63054; and *Aspergillus* sp., e.g. *Aspergillus niger*, such as *Aspergillus niger* van Tieghem. In one embodiment, a first microorganism is an organism capable of producing at least one enzyme, and further capable of producing protein biomass and an aroma compound, preferably selected from *Aspergillus* sp., more preferably *Aspergillus oryzae.*

In one embodiment, a first microorganism is an organism capable of producing at least one enzyme, and further capable of producing an aroma compound and protein biomass, e.g. *Aspergillus* sp. such as *Aspergillus oryzae*. In one embodiment, a first microorganism is co-cultivated with an organism producing protein biomass, e.g. microalgae such as a *Chlorella* microalga. In one embodiment, in said step b) of cultivating a first microorganism, at least one enzyme and an enzymatically treated first substrate is produced; and, optionally, protein biomass, microbial lipids, and/or aroma compounds, preferably protein biomass and/or aroma compounds, are produced.

In one embodiment, cultivating a first microorganism comprises subjecting said first microorganism to suitable growth conditions. In one embodiment, the terms "cultivating" and "growing" are used interchangeably. In one embodiment, cultivating a first microorganism comprises contacting said first microorganism with said first substrate. In one embodiment, the first substrate is the growth substrate for the first microorganism. In one embodiment, in said step b) of cultivating a first microorganism, said first microorganism produces at least one enzyme, preferably an enzyme mix, with enzymatic activity specific for the first substrate, and optionally further produces protein biomass and/or aroma compounds. In one embodiment, the first microorganism is co-cultivated with microalgae that produce protein biomass, microbial lipids, and/or aroma compounds. In one embodiment, if the method of the invention is a method for producing microbial lipids and protein biomass and/or aroma compounds, the first microorganism is selected such that the first microorganism is capable of producing protein biomass and/or aroma compounds, in addition to producing said at least one enzyme, and/or the first microorganism is co-cultivated with one or more microalgae capable of producing protein biomass and/or aroma compounds. In one embodiment, when referring to a microorganism producing an enzymatically treated substrate, it is meant that the microorganism produces one or more enzymes, preferably an enzyme mix, which enzymatically treat(s) the substrate; for example, it is meant that the microorganism indirectly produces an enzymatically treated substrate by producing said at least one enzyme, preferably said enzyme mix, which enzymatically treats the substrate. In one embodiment, the terms "at least one" and "one or more" are used interchangeably.

The term "filamentous fungi", as used herein, relates to fungi with filamentous structure, particularly with hyphae. In one embodiment, filamentous fungi are selected from *Ceratocystis* sp., e.g. *Ceratocystis fimbriata, Ceratocystis moniliformis*, and *Ceratocystis paradoxa* such as *Ceratocystis paradoxa* CBS 374.83 or *Ceratocystis paradoxa* DSM 63054, preferably *Ceratocystis paradoxa; Trichoderma* sp., e.g. *Trichoderma reesei* and *Trichoderma harzianum; Aspergillus* sp., e.g. *Aspergillus oryzae, Aspergillus tubingensis, Aspergillus terreus*, and *Aspergillus niger* such as *Aspergillus niger* van Tiegheim ATCC 10535; *Neurospora* sp., e.g. *Neurospora intermedia; Monascus* sp., e.g. *Monascus purpureus; Rhizopus* sp., e.g. *Rhizopus oryzae; Fusarium* sp., e.g. *Fusarium venenatum; Thermomyces* sp.; *Penicillium* sp.; *Aureobasillium* sp.; *Ischnoderma* sp., e.g. *Ischnoderma benzoinum; Polyporus* sp., e.g. *Polyporus durus; Pycnoporus* sp., e.g. *Pycnoporus cinnabarinus; Phanerochaete* sp., e.g. *Phanerochaete chrysosporium*; and *Xylaria* sp; preferably selected from *Ceratocystis* sp.,

*Trichoderma* sp., *Aspergillus* sp., and *Fusarium* sp. In one embodiment, said filamentous fungi are selected from *Aspergillus* sp., preferably *Aspergillus niger*, more preferably *Aspergillus niger* van Tiegheim ATCC 10535; and *Ceratocystis* sp., preferably *Ceratocystis paradoxa*, more preferably *Ceratocystis paradoxa* CBS 374.83.

The term "bacteria", as used herein in the context of step b), relates to any bacteria capable of producing at least one enzyme when cultivated with a first substrate. In one embodiment, said bacteria are selected from *Clostridium* sp., e.g. *Clostridium stercorarium, Clostridium beijerinckii*, and *Clostridium acetobutylicum; Halobacillus* sp., e.g. *Halobacillus trueperi* and *Halobacillus karajensis; Halomonas* sp., e.g. *Halomonas meridiana* and *Halomonas elongata; Rhodothermus* sp., e.g. *Rhodothermus marinus; Streptomyces* sp., e.g. *Streptomyces griseus, Streptomyces olivochromogenes, Streptomyces griseorubens*, and *Streptomyces matensis*; and *Bacillus* sp., e.g. *Bacillus nato, Bacillus subtilis, Bacillus licheniformis*, and *Bacillus stearothermophilus.*

The term "at least one enzyme", as used herein, relates to one or more enzymes, preferably an enzyme mix. In one embodiment, said at least one enzyme has an activity targeting said first and/or second substrate, and/or targeting at least one component of said first and/or second substrate. In one embodiment, said at least one enzyme is capable of enzymatically treating a substrate to provide a growth medium and/or components for a growth medium. In one embodiment, said at least one enzyme is capable of enzymatically treating a substrate to convert said substrate into nutrients and/or to release nutrients from said substrate, preferably nutrients for the growth of a first and/or second microorganism. In one embodiment, said at least one enzyme acts on said substrate such that the substrate becomes a suitable growth medium for said first microorganism and/or second microorganism. In one embodiment, said at least one enzyme contains one or several activities selected from enzyme activities of cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; and laminarinase; optionally selected from enzyme activities of cellulase; lichenase; xylanase; arabinanase; amylase, e.g. α-amylase; limit dextrinase; pullulanase; protease; galactanase; mannanase; rhamnogalacturonan hydrolase; and rhamnogalacturonan lyase. In one embodiment, said at least one enzyme is any of cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; laminarinase; and combinations thereof. In one embodiment, said at least one enzyme is an enzyme mix. In one embodiment, an enzyme mix comprises at least two or three, preferably at least five, more preferably at least six, even more preferably at least seven enzymes. In one embodiment, an enzyme mix comprises at least two or three, preferably at least five, more preferably at least six, even more preferably at least seven enzymes selected from cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; and laminarinase. In one embodiment, said at least one enzyme is adapted to said substrate, i.e. by contacting said first microorganism with said substrate, said first microorganism produces enzymes specifically acting on said substrate. For example, if bread residue(s) is used as said substrate, the at least one enzyme produced in step b) of the method of the invention and/or the composition of the invention may comprise

- cellulase; amylase; hemicellulase; limit dextrinase e.g. malt limit dextrinase; and pectinase; and/or
- cellulase; lichenase; xylanase; arabinanase; amylase, e.g. α-amylase; limit dextrinase; pullulanase; protease; galactanase; and mannanase; and/or
- cellulase; xylanase; arabinanase; amylase, e.g. α-amylase; limit dextrinase; pullulanase; galactanase; mannanase; rhamnogalacturonan hydrolase; and rhamnogalacturonan lyase.

In one embodiment, the composition of the invention is the at least one enzyme produced in step b) of the method of the invention. In one embodiment, the at least one enzyme produced in step b) of the method of the invention is a composition of the invention. In one embodiment, said at least one enzyme has food-grade. In one embodiment, said at least one enzyme is a food-grade enzyme or food-grade enzyme composition. In one embodiment, said at least one enzyme comprises or consists of at least one food-grade enzyme. In one embodiment, if said first substrate is a food-grade food residue(s), said at least one enzyme is a food-grade enzyme or food-grade enzyme composition.

In one embodiment, the term "enzymatically treated first substrate", as used herein, relates to a first substrate that has been contacted with said at least one enzyme produced by said first microorganism. In one embodiment, the enzymatically treated first substrate, or components thereof, is/are used as a growth medium for said second microorganism or is/are used as supplement(s) in a growth medium for said second microorganism. In one embodiment, said medium used in step d) comprises or consists of the enzymatically treated first substrate and/or the enzymatically treated second substrate, and/or comprises a consists of components, preferably nutrients, of said enzymatically treated first substrate and/or the enzymatically treated second substrate. In one embodiment, an enzymatically treated first substrate is a hydrolysate of said first substrate.

The term "microalgae", as used herein in the context of step b), relates to any microalgae capable of producing protein biomass, microbial lipids, and/or aroma compounds. In one embodiment, said microalgae used in step b) are selected from *Chlorella* sp., e.g. *Chlorella vulgaris* and *Chlorella* protothecoides; *Scenedesmus* sp, e.g. *Scenedesmus obliquus; Dunaliella* sp, e.g. *Dunaliella salina; Haematococcus* sp, e.g. *Haematococcus pluvialis; Crypthecodinium* sp, e.g. *Crypthecodinium cohnii; Schizochytrium* sp, e.g. *Schizochytrium limacinum*; and *Tetraselmis* sp, e.g. *Tetraselmis chui*; preferably are selected from *Chlorella* sp. and *Scenedesmus* sp. In one embodiment, step b) comprises co-cultivating said first microorganism with microalgae to obtain, in addition to said at least one enzyme and said enzymatically treated first substrate produced by said first microorganism, protein biomass, microbial lipids, and/or aroma compounds produced by said microalgae. Such protein biomass, microbial lipids, and/or aroma compounds produced by said microalgae can be used to prepare foodstuff comprising said protein biomass, microbial lipids, and/or aroma compounds. In one embodiment, a microalga used in step b) to produce protein biomass is selected from *Chlorella vulgaris, Dunaliella salina, Haematococcus pluvialis* and *Scenedesmus obliquus*. In one embodiment, a microalga capable of producing protein biomass is selected from *Chlorella vulgaris, Dunaliella salina, Haematococcus*

*pluvialis* and *Scenedesmus obliquus*. In one embodiment, a microalga used in step b) to produce an aroma compound is selected from *Crypthecodinium cohnii, Schizochytrium limacinum, Tetraselmis chui, Chlorella vulgaris*, and *Chlorella* protothecoides. In one embodiment, a microalga capable of producing an aroma compound is selected from *Crypthecodinium cohnii, Schizochytrium limacinum, Tetraselmis chui, Chlorella vulgaris*, and *Chlorella* protothecoides.

In one embodiment, said cultivating a first microorganism in step b) is performed at a temperature in the range of from 25° C. to 37° C. In one embodiment, said cultivating a first microorganism of step b) is performed at a pH in the range of from pH 4 to pH 8. In one embodiment, said cultivating a first microorganism of step b) is performed for 2 to 12 days, preferably for 3 to 10 days. In one embodiment, said cultivating a first microorganism of step b) is performed with $pO_2$>20%. In one embodiment, said cultivating a first microorganism of step b) is performed under agitation, preferably under stirring with a rotational speed in the range of from 100 to 800 rpm. For example, a paddle stirrer may be used. In one embodiment, said cultivating a first microorganism of step b) is performed at a temperature in the range of from 25° C. to 37° C., at a pH in the range of from pH 4 to pH 8, for 3 to 10 days, with $pO_2$>20%, under agitation, preferably under stirring with a rotational speed in the range of from 100 to 800 rpm.

In one embodiment, said cultivating a first microorganism in step b) comprises cultivating said first microorganism for 2 to 12 days, preferably for 3 to 10 days, at a temperature in the range of from 25° C. to 37° C., at a pH in the range of from pH 4 to pH 8, and/or at a dissolved oxygen ($pO_2$) $pO_2$>20%.

In one embodiment, step b) of the method of the invention comprises cultivating a first microorganism selected from filamentous fungi and bacteria with said first substrate, and thereby allowing said first microorganism to produce at least one enzyme, an enzymatically treated first substrate, and protein biomass and/or aroma compounds; optionally further comprises co-cultivating one or more microalgae with said first microorganism, and thereby allowing said one or more microalgae to produce protein biomass, microbial lipids, and/or aroma compounds.

In one embodiment, the term "co-cultivating one or more microalgae with said first microorganism", as used herein, relates to a combined cultivation of said first microorganism with said microalgae, e.g. a cultivation in the same vessel. In one embodiment, the co-cultivation comprises subjecting said first microorganism and said microalgae to culture conditions suitable for both the first microorganism and the microalgae. In one embodiment, if culture conditions suitable for the first microorganism differ from culture conditions suitable for the microalgae, said co-cultivating in step b), if present, comprises subjecting said first microorganism and microalgae subsequently to culture conditions suitable for the first microorganism and culture conditions suitable for the microalgae, or vice versa.

In one embodiment, said method comprises a step of obtaining protein biomass and/or aroma compounds produced by said first microorganism in step b); and, optionally, obtaining protein biomass, microbial lipids, and/or aroma compounds produced by said one or more microalgae. In one embodiment, if step b) comprises co-cultivating one or more microalgae with said first microorganism, said method comprises a step of obtaining protein biomass, microbial lipids, and/or aroma compounds produced by said one or more microalgae. In one embodiment, the terms "obtaining" and "harvesting" are used interchangeably. In one embodiment, harvesting said protein biomass and/or said aroma compounds is performed using any of centrifugation, filtration, distillation, organophilic pervaporation, solid-phase micro extraction, and combinations thereof. In one embodiment, harvesting said microbial lipids produced by said microalgae in step b) comprises any of centrifugation, solvent extraction e.g. with hexane, solvent-free extraction e.g. comprising enzymatic hydrolysis of the microalgae cell walls followed by centrifugation such as semicontinous centrifugation of the disrupted cells, cold pressing, demulsification, and any combination thereof; preferably comprising any of centrifugation, solvent-free extraction e.g. comprising enzymatic hydrolysis of the microalgae cell walls followed by centrifugation such as semicontinous centrifugation of the disrupted cells, cold pressing, and any combination thereof. In one embodiment, harvesting said microbial lipids produced by said microalgae in step b) is without solvent-based extraction and chemicals-based demulsification. For example, protein biomass is harvested using centrifugation and/or filtration. For example, aroma compounds are harvested using distillation, organophilic pervaporation, solid-phase micro extraction, and combinations thereof.

In one embodiment, the term "pretreating a second substrate", as used herein, relates to contacting said second substrate with said at least one enzyme, preferably enzymatically treating said second substrate with said at least one enzyme. In one embodiment, by pretreating said second substrate with the at least one enzyme, said second substrate is converted into and/or releases compounds that allow the second microorganism to grow, preferably nutrients, e.g. the second substrate is converted into a growth medium and/or into components for a growth medium for said second microorganism. In one embodiment, pretreating said second substrate with said at least one enzyme comprises contacting said second substrate with said at least one enzyme, preferably an enzyme mix, for 6-72 h, preferably 12-48 hours, more preferably 20-30 hours; e.g. at a temperature in the range of from 20-80° C., preferably 30-60° C., and/or at a pH in the range of from pH 3 to pH 9, preferably pH 4 to pH 7. In one embodiment, pretreating a second substrate with said at least one enzyme comprises or consists of enzymatically treating said second substrate with said at least one enzyme.

In one embodiment, said pretreating a second substrate in step c), if step c) is present, is performed at a temperature in the range of from 30° C. to 80° C. In one embodiment, said pretreating a second substrate of step c) is performed at a pH in the range of from pH 4 to pH 9. In one embodiment, said pretreating a second substrate of step c) is performed under agitation, preferably under stirring with a rotational speed in the range of from 200 to 800 rpm. In one embodiment, said pretreating a second substrate of step c) is performed at a temperature in the range of from 30° C. to 80° C., at a pH in the range of from pH 4 to pH 9, under agitation, preferably under stirring with a rotational speed in the range of from 200 to 800 rpm. In one embodiment, said pretreating a second substrate in step c), if present, comprises treating said second substrate with said at least one enzyme, preferably an enzyme mix, optionally the composition of the invention, for 6-72 h, preferably 12-48 hours, more preferably 20-30 hours; e.g. at a temperature in the range of from 20° C. to 80° C., preferably 30° C. to 60° C., and/or at a pH in the range of from pH 3 to pH 9, preferably pH 4 to pH 7. In one embodiment, said pretreating a second substrate in step c), if present, comprises treating said second substrate with said at least one enzyme in a liquid, e.g. a medium comprising a buffer system.

In one embodiment, said method comprises step c) of obtaining said at least one enzyme and pretreating said second substrate with said at least one enzyme, wherein said pretreating comprises contacting said second substrate with said at least one enzyme in the form of a liquid enzyme preparation obtained, preferably directly obtained, from culturing said first microorganism, or in the form of a freeze-dried enzyme preparation, optionally a freeze-dried enzyme preparation reconstituted in solution. In one embodiment, said obtaining said at least one enzyme of step c) comprises obtaining said at least one enzyme in the form of liquid or in the form of a freeze-dried enzyme preparation. In one embodiment, such freeze-dried enzyme preparation of said at least one enzyme is dissolved prior to said pretreating a second substrate with said at least one enzyme.

In one embodiment, the term "enzymatically treated second substrate", as used herein, relates to a second substrate that has been contacted with said at least one enzyme produced by said first microorganism. In one embodiment, the enzymatically treated second substrate, or components thereof, is/are used as a growth medium for said second microorganism or is/are used as supplement(s) in a growth medium for said second microorganism. In one embodiment, an enzymatically treated second substrate is a hydrolysate of said second substrate.

In one embodiment, the term "of the same type", as used herein, relates to the first substrate and the second substrate comprising or consisting of the same type or substantially same type of food residue(s), e.g. both the first substrate and the second substrate are bakery product food residue(s). For example, first and second substrates of the same type are derived from the same source, e.g. the same batch of food residue(s), and/or have the same or similar composition. In one embodiment, when the first substrate and the second substrate are of the same type, the first substrate and the second substrate are identical. In one embodiment, the composition of the first substrate and the composition of the second substrate is at least 50%, preferably at least 70%, more preferably at least 90% similar; i.e. the components, and optionally their concentrations, have a similarity of at least 50%, preferably at least 70%, more preferably at least 90%. In one embodiment, when the first substrate and the second substrate are of the same type, both the first substrate and the second substrate are bakery food residue(s), e.g. bread, bread rolls, biscuit, muffins, cookies, or cake; fruit food residue(s), e.g. fruit pulp, fruit peel, or fruit juice; vegetable food residue(s), e.g. vegetable peel, vegetable pulp, or vegetable juice; milling food residue(s), e.g. bran or bran flour; fish food residue(s), e.g. fish processing residue; sea food residue(s), e.g. sea food processing residue; brewer's spent grain; cereal food residue(s), e.g. rice, wheat, millet, or maize; restaurant food residue(s), e.g. restaurant leftovers; animal product food residue(s), e.g. milk or cheese; supermarket food residue(s), e.g. food with expired expiration date; or any combination thereof. In a preferred embodiment, when the first substrate and the second substrate are of the same type, both the first substrate and the second substrate are bakery food residue(s), preferably bread food residue(s).

The term "second microorganism", as used herein, relates to an oleaginous microorganism, preferably selected from oleaginous yeasts, oleaginous fungi, oleaginous bacteria, and oleaginous microalgae. Oleaginous microorganisms are known to a person skilled in the art. Oleaginous yeasts, oleaginous fungi, oleaginous bacteria, and oleaginous microalgae are microorganisms typically capable of producing microbial lipids.

In one embodiment, said oleaginous yeasts are selected from *Cutaneotrichosporon* sp., e.g. *Cutaneotrichosporon oleaginosus; Trichosporon* sp., e.g. *Trichosporon oleaginosus, Trichosporon capitatu*, and *Trichosporon asahii; Rhodospirillum* sp.; *Rhodosporidium* sp., e.g. *Rhodosporidium toruloides; Rhodosporon* sp.; *Candida* sp., e.g. *Candida viswanathii* and *Candida freyschussii; Cryptococcus* sp., e.g. *Cryptococcus curvatus; Lipomyces* sp., e.g. *Lipomyces starkeyi; Yarrowia* sp., e.g. *Yarrowia lipolytica; Rhodotorula* sp., e.g. *Rhodotorula graminis, Rhodotorula gracilis*, and *Rhodotorula glutinis*; and *Apiotrichum* sp., e.g. *Apiotrichum curvarum*. In a preferred embodiment, said oleaginous yeasts are selected from *Cutaneotrichosporon* sp., preferably *Cutaneotrichosporon oleaginosus*. In one embodiment, the oleaginous yeast is not *Rhodosporidium toruloides*. In one embodiment, said *Rhodosporidium* sp. do not include *Rhodosporidium toruloides*. In one embodiment, if said second microorganism is a *Rhodosporidium* sp., the *Rhodosporidium* sp. is not *Rhodosporidium toruloides*. In one embodiment, if said oleaginous yeast is a *Rhodosporidium* sp., the *Rhodosporidium* sp. is not *Rhodosporidium toruloides*.

In one embodiment, said oleaginous fungi are selected from *Cunninghamella* sp., e.g. *Cunninghamella echinulate; Aspergillus* sp., e.g. *Aspergillus oryzae, Aspergillus tubingensis, Aspergillus terreus*, and *Aspergillus niger; Neurospora* sp., e.g. *Neurospora intermedia; Monascus* sp., e.g. *Monascus purpureus; Rhizopus* sp., e.g. *Rhizopus oryzae; Fusarium* sp., e.g. *Fusarium venenatum; Mucor* sp., e.g. *Mucor moelleri; Mortierella* sp., e.g. *Mortariella isabellina* and *Mortierella alpine*, preferably *Mortierella alpine*; and *Humicola* sp.

In one embodiment, said oleaginous bacteria are selected from *Rhodococcus* sp.; *Acinetobacter* sp.; and *Bacillus* sp.

In one embodiment, said oleaginous microalgae are selected from *Chlorella* sp., *Pseudochlorococcum* sp., *Nannochloris* sp., *Nannochloropsis* sp., *Isochrysis* sp., *Tribonema* sp., *Dunaliella* sp., *Ankistrodesmus* sp., *Botryococcus* sp., *Pavlova* sp., *Scenedesmus* sp., *Skeletonema* sp., and *Nitzschia* sp.

In one embodiment, the second microorganism is an oleaginous yeast, preferably selected from *Cutaneotrichosporon oleaginosus, Trichosporon oleaginosus, Trichosporon capitatu, Trichosporon asahii, Lipomyces starkeyi, Rhodosporidium toruloides, Yarrowia lipolytica, Rhodotorula graminis, Rhodotorula gracilis, Rhodotorula glutinis, Apiotrichum curvarum, Cryptococcus curvatus, Candida viswanathii*, and *Candida freyschussii*; e.g. *Cutaneotrichosporon oleaginosus*. In one embodiment, the second microorganism is not *Rhodosporidium toruloides*. For example, the second microorganism may be an oleaginous yeast selected from *Cutaneotrichosporon oleaginosus, Trichosporon oleaginosus, Trichosporon capitatu, Trichosporon asahii, Lipomyces starkeyi, Yarrowia lipolytica, Rhodotorula graminis, Rhodotorula gracilis, Rhodotorula glutinis, Apiotrichum curvarum, Cryptococcus curvatus, Candida viswanathii*, and *Candida freyschussii*. In a preferred embodiment, the second microorganism is an oleaginous yeast, preferably selected from *Cutaneotrichosporon* sp., more preferably *Cutaneotrichosporon oleaginosus*. In accordance with one embodiment according to the present invention, the oleaginous microorganism that is used in the method according to the present invention is selected from oleaginous yeasts, oleaginous fungi, oleaginous bacteria, and oleaginous microalgae; preferably is an oleaginous yeast. In a preferred embodiment, said oleaginous microorganism/yeast is *Cutaneotrichosporon oleaginosus* (*C. oleaginosus*).

The term "medium comprising said enzymatically treated substrate", as used herein, relates to a medium comprising an enzymatically treated first substrate and/or an enzymatically treated second substrate and/or comprising components of said enzymatically treated first and/or second substrate; e.g. a medium comprising or consisting of a hydrolysate of a first substrate obtained in step b) and/or a hydrolysate of a second substrate obtained in step c). In one embodiment, said enzymatically treated first substrate and/or components of said enzymatically treated first are a hydrolysate obtained in step b), preferably a hydrolysate of said first substrate. In one embodiment, said enzymatically treated second substrate and/or components of said enzymatically treated second are a hydrolysate obtained in step c), preferably a hydrolysate of said second substrate. In one embodiment, the medium used in step d) comprises a hydrolysate of said first substrate and/or a hydrolysate of said second substrate. In one embodiment, said medium is a growth medium for said second microorganism. In one embodiment, the terms "medium" and "growth medium" are used interchangeably. In one embodiment, a medium comprises the components/nutrients e.g. that allow an organism, e.g. the second microorganism, to grow. In one embodiment, a medium comprises at least components of an enzymatically treated first substrate and/or an enzymatically treated second substrate, and optionally further comprises an additional carbon source, nitrogen source, organic acid e.g. acetic acid, trace metal, and/or vitamin. In this context, "additional" means that the medium may comprise a carbon source, nitrogen source, organic acid, trace metal, and/or vitamin derived from said enzymatically treated first substrate and/or an enzymatically treated second substrate, and, additionally, a further carbon source, nitrogen source, organic acid, trace metal, and/or vitamin not derive from said enzymatically treated first substrate and/or an enzymatically treated second substrate. In one embodiment, said carbon source is a food-grade carbon source. In one embodiment, the term "medium comprising an enzymatically treated substrate" relates to a medium comprising the enzymatically treated substrate, e.g. the enzymatically treated first substrate of step b) or the enzymatically treated second substrate of step c), and/or to a medium comprising components of the enzymatically treated substrate(s). For example, components of the enzymatically treated substrate may be harvested, and said components may be incorporated into a medium or an enzymatically treated substrate may be directly used as a medium. For example, the enzymatically treated first substrate obtained in step b) and/or the enzymatically treated second substrate obtained in step c) may be directly used as the medium used in step d). The enzymatically treated first substrate and the enzymatically treated second substrate may be mixed to provide a medium for step d). In one embodiment, the medium/media used in step b) and/or c) comprise the enzymatically treated first and second substrate, respectively, and is/are used as the medium for cultivating the second microorganism in step d). In one embodiment, the medium used in step d) comprises or consists of a medium used in step b) comprising said enzymatically treated first substrate, and/or comprises or consists of a medium used in step c) comprising said enzymatically treated second substrate. In one embodiment, the terms "enzymatically treated first substrate" and "hydrolysate of a first substrate" are used interchangeably. In one embodiment, the terms "enzymatically treated second substrate" and "hydrolysate of a second substrate" are used interchangeably. In one embodiment, such hydrolysates, e.g. the hydrolysate of the first substrate and/or the hydrolysate of the second substrate, are used as a medium for growing the second microorganism in step d). In one embodiment, the cell culture broth of step b) and/or c) comprising an enzymatically treated substrate is used as a medium for step d). In one embodiment, after step b) or, if step c) is present, after step c), the second microorganism is cultivated in step d) in a medium used in step b) or c), respectively. For example, the second microorganism may be added to the vessel, e.g. cell culture vessel, in which step b) and/or step c) has been performed.

In one embodiment, the enzymatically treated first substrate used in step d) comprises a medium used in step b); wherein, optionally, said medium has been filtered and/or centrifuged. In one embodiment, the enzymatically treated second substrate used in step d) comprises a liquid, e.g. medium, used in step c); wherein, optionally, said liquid has been filtered and/or centrifuged. In one embodiment, the medium used in step d) is the medium used in step b) and/or step c); wherein, optionally, said medium has been filtered and/or centrifuged. In one embodiment, a liquid, e.g. medium, used in step b) and/or c) is transferred to step d) and used as the medium in step d).

In one embodiment, said enzymatically treated first substrate produced in step b) is centrifuged prior to using said enzymatically treated first substrate in a medium in step d). In one embodiment, a growth medium used in step b) comprising the produced enzymatically treated first substrate is centrifuged, and a supernatant of such centrifugation is used as the medium for step d) or as a component of the medium for step d). In one embodiment, said enzymatically treated second substrate produced in step c) is centrifuged prior to using said enzymatically treated second substrate in a medium in step d). In one embodiment, a medium used in step c) comprising the produced enzymatically treated second substrate is centrifuged, and a supernatant of such centrifugation is used as the medium for step d) or as a component of the medium for step d). For example, such centrifugation may be a centrifugation in the range of from 5.000 rpm to 20.000 rpm, e.g. 14.000 rpm, for 1 to 60 min, e.g. for 20 min. In one embodiment, using such centrifugation, protein biomass can be harvested by separating the biomass from the supernatant comprising the enzymatically treated substrate.

In one embodiment, said medium further comprises an additional carbon source, nitrogen source, organic acid, trace metal, and/or vitamin. In one embodiment, said medium comprises any of carbohydrates; such as monosaccharides, preferably pentoses or hexoses, more preferably glucose, xylose, mannitol, arabinose; and oligosaccharides; protein hydrolysates such as oligo-amino acids and amino acids or other peptidic hydrolysates; fatty acids; organic acids, preferably acetic acid; minerals; vitamins and trace elements, and combinations thereof. In one embodiment, the additional carbon source is selected from sugars, glycerol, sugar alcohols, sugar acids, fatty acids, fatty alcohols, and fatty esters. In one embodiment, the nitrogen source is selected from urea, protein hydrolysates, amino acids, inorganic nitrite salts. In one embodiment, the trace metal is selected from V, Mo, Cu, and Fe. In one embodiment, the vitamin is selected from vitamin C, vitamin B, vitamin A, and vitamin E. In one embodiment, said additional carbon source, nitrogen source, organic acid, trace metal, and/or vitamin have/has food-grade.

In one embodiment, said carbon source is selected from the group comprising carbohydrates; amino acids; fatty acids; preferably monosaccharides, preferably pentoses or hexoses, more preferably glucose, xylose and/or mannitol; oligosaccharides; hydrolysates of animal tissues, plant tissues or of microorganisms; and combinations of any of the foregoing, wherein more preferably, said carbon source is glucose. In one embodiment, the concentration of said carbon source in said medium is in a range from 50 to 400 mM, preferably 200 to 300 mM. Said glucose may be used alone or may e.g. be used in combination with suitable hydrolysates, such as peptone, tryptone etc. In one embodiment, the hydrolysate is an algal hydrolysate, a lignocellulosic hydrolysate, a vegetable hydrolysate, a marine biomass hydrolysate, such as a hydrolysate of marine macro- and micro-algae, a corn hydrolysate, a wheat hydrolysate or other hydrolysate. In some embodiments of the method according to the present invention which involve a recycling step, the hydrolysate may also be a microbial hydrolysate, e.g. a yeast hydrolysate, derived from hydrolysis of the oleaginous microorganism, e.g. yeast itself, preferably after such hydrolysate has been used to produce lipids.

In one embodiment, the weight ratio of carbon to nitrogen (C:N) in the medium is (100-200): 1, especially if it is a limited nitrogen medium. In another embodiment, the weight ratio of carbon to nitrogen (C:N) in the medium is (10-100): 1, preferably (10-50): 1, especially when it is not a nitrogen limited medium. In one embodiment, the medium is a nitrogen-rich medium. The weight ratios indicated above and further below are weight ratios in the starting medium, i.e. when step d) begins. As used herein, the term "nitrogen-rich medium" refers to a medium that is not a limited nitrogen medium. In one embodiment, a "nitrogen-rich medium" refers to a medium in which the weight ratio of carbon to nitrogen (C:N) is <100, preferably ≤80, more preferably 25-80.

In one embodiment, said medium used in step d) is a nitrogen-rich medium. In one embodiment, said medium used in step d) further comprises a nitrogen source, preferably in the form of a protein hydrolysate, such as peptone, tryptone or other peptidic hydrolysate, wherein, preferably, said peptidic hydrolysate comprises animal tissue, plant tissue and/or components of said oleaginous microorganism. In one embodiment, a nitrogen source is selected from protein hydrolysate, such as peptone, tryptone or other peptidic hydrolysate, wherein, preferably, said peptidic hydrolysate comprises animal tissue, plant tissue and/or components of said oleaginous microorganism. Without wishing to be bound by any theory, the present inventors believe that the presence of such additional nitrogen source allows to increase the production of lipids and biomass, in total.

In one embodiment, said organic acid is selected from the group comprising acetic acids, malonic acid, oxalic acid, citric acid, propionic acid, valeric acid, acrylic acid, crotonic acid, butyric acid, isobutyric acid, isovaleric acid, 3-hydroxybutyric acid, 3-hydroxypropionic acid, 2-hydroxybutyric acid, lactic acid and the respective salt(s) of such acid, as well as mixtures of any of the foregoing organic acids. Preferably, said organic acid is acetic acid or acetate. In one embodiment, said organic acid is acetic acid or acetate only; in another embodiment said organic acid is a combination of acetic acid or acetate, with any of the other aforementioned organic acids. It should be noted that the term "organic acid", as used herein is meant to encompass the respective organic acid irrespective of its degree of protonation, i.e. it is meant to encompass said acid in its protonated state(s) as well as deprotonated state(s), e.g. when in aqueous solution at a pH at which it is protonated or deprotonated, respectively, depending on the respective pKa-value(s). The term "organic acid", as used herein, is also meant to encompass salt(s) of the organic acid, e.g. the respective metal salts of such organic acid.

Examples of such metal salts are the alkali salts or earth alkaline salts of the respective organic acid. The salts may be in their dissociated form or undissociated form. The term "mixtures of organic acids", as used herein is meant to encompass mixtures of organic acids in their respective acid form, i.e. with other organic acids, mixtures of organic acids in their acid form with other organic acids in their salt form, and mixtures of salts of organic acids with other salts of organic acids. It should also be noted that the term "organic acid", as used herein, does not encompass fatty acids or amino acids. The phrase "a carbon source and an organic acid", as used herein, implies that the "carbon source" is different from the "organic acid". Hence the two entities are chemically different. In one embodiment, the concentration of said organic acid is in a range of from 20 to 200 mM, preferably 30 to 100 mM. In one embodiment, the medium used in step d) is supplemented with an organic acid.

In one embodiment, said cultivating a second microorganism of step d) is performed at a temperature in the range of from 10° C. to 37° C., preferably 18° C. to 33° C. In one embodiment, said cultivating a second microorganism of step d) is performed at a pH in the range of from pH 3 to pH 9. In one embodiment, said cultivating a second microorganism of step d) is performed for 1 to 12 days, preferably for 2 to 10 days. In one embodiment, said cultivating a second microorganism of step d) is performed with $pO_2$>20%. In one embodiment, said cultivating a second microorganism of step d) is performed under agitation, preferably under stirring with a rotational speed in the range of from 20 to 1000 rpm, e.g. 50 to 800 rpm. For example, a paddle stirrer may be used. In one embodiment, said cultivating a second microorganism of step d) is performed at a temperature in the range of from 10° C. to 37° C., preferably 18° C. to 33° C., at a pH in the range of from pH 3 to pH 9, for 1 to 12 days, preferably for 2 to 10 days, with $pO_2$>20%, under agitation, preferably under stirring with a rotational speed in the range of from 20 to 1000 rpm, e.g. 50 to 800 rpm. In one embodiment, said cultivating a second microorganism of step d) comprises cultivating said second microorganism for 1 to 12 days, preferably for 2 to 10 days, at a temperature in the range of from 10° C. to 37° C., preferably 18° C. to 33° C., at a pH in the range of from pH 3 to pH 9, and/or at a dissolved oxygen ($pO_2$) $pO_2$>20%, preferably in a medium comprising any of an enzymatically treated first substrate or components thereof, an enzymatically treated second substrate or components thereof, YPD, YNB, Sabouraud bouillong, and any combination thereof.

In one embodiment, the method is suitable for producing lipids with a content of >60% unsaturated fatty acids with respect to the total fatty acids content and/or a pour point in a range of <10° C., e.g. from 9° C. to 5° C., such as for example approximately 5° C. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 10-20° C., dissolved oxygen content 10-30% and/or addition of crotonic acid (0-10% of total organic acid), and thereby allowing said oleaginous microorganism to produce microbial lipids, which are characterized by a "pour point"

in a range of <10° C., e.g. from 9° C. to 5° C., such as for example ca. 5° C., and/or an unsaturated fatty acid content of >60% with respect to the total fatty acid content. The "pour point", as used herein, is typically determined in accordance with any of the following standards: DIN51597, DIN EN 23015:1994-05, DIN ISO 3015:1982-10, DIN ISO 3016:1982-10, ASTM D97, ASTM D5985, preferably using DIN ISO 3016.

During culturing of microorganisms for the production of microbial oils, there is an offset either in lipid productivity or biomass productivity for production of microbial oil. Conventionally lipids are generated in a two phase system comprising a first step for biomass production under non-limiting conditions, followed by a nutrient limiting phase during which biomass growth is stopped and only lipids are accumulated. Under these conditions lipid productivity does not exceed 70% w/w. Surprisingly, this invention discloses a completely new route for lipid production wherein biomass growth and lipid accumulation can be achieved simultaneously. This provides an option for biomass and lipid yield exceeding 200 g $L^{-1}$ biomass containing in excess of 85% lipid w/w.

In one embodiment, the oleaginous microorganism is grown in a medium comprising said enzymatically treated substrate and optionally further comprising any of a carbon source, nitrogen source, organic acid, trace metal, and/or vitamin. Depending on the pH at which said medium is, the organic acid is dissociated/deprotonated in which case it is present as salt/carboxylate anionic form, or it is non-dissociated in which case it is present as organic acid in its protonated form. In one embodiment, the medium in which said oleaginous microorganism is grown in step d) comprises said enzymatically treated substrate. In one embodiment, the terms "cultivating" and "growing" are used synonymously. In one embodiment, when referring to an "enzymatically treated substrate", such term relates to an "enzymatically treated first substrate" and/or an "enzymatically treated second substrate". Without wishing to be bound by any theory, the present inventors believe that the presence of organic acid, e.g. acetic acid/acetate allows to even further increase the lipid productivity, whereas the presence of a carbon source allows an increase in the total biomass. It should be noted that the "carbon source" and the organic acid, as defined above, are two different entities which are different from each other.

In one embodiment, the term "a purely enzymatic treatment of said cultivated second microorganism without any solvent-based extraction or chemicals-based demulsification" is meant to refer to an enzymatic treatment of said oleaginous microorganism in which there is a) no extraction using one or several solvents or b) no demulsification using one or several (suitable) chemical reagents or c) neither of a) and b). Preferably such term is meant to refer to an enzymatic treatment devoid of any exposure to an extracting solvent and devoid of any exposure to a demulsifying chemical reagent. The term is also meant to exclude the performance of any other pretreatment of said grown oleaginous microorganism. It should be noted that in embodiments of the invention, the "purely enzymatic treatment" excludes the performance of any pretreatment of the grown oleaginous microorganism, which pretreatment may be chemical (using one or several chemical reagents to which the grown oleaginous microorganism would be exposed) or physical (such as the change of a physical condition, e.g. temperature, pressure, ultrasound, light, irradiation with electromagnetic radiation etc.).

In one embodiment, said purely enzymatic treatment of said grown oleaginous microorganism is a treatment of said microorganism with a hydrolase, alone, or in combination with/followed by a protease. In one embodiment, said hydrolase has been obtained from a fungus, preferably a filamentous fungus, more preferably a fungi from the Genus *Trichoderma, Aspergillus, Penicillium, Aureobasilium* and *Fusarium*. In one embodiment, said hydrolase is obtained from a fungus that has been cultured in the presence of an inducing system, wherein, preferably, said inducing system is a component of said oleaginous microorganism, more preferably one or several cell-wall components of said oleaginous microorganism used for producing microbial lipids, so as to obtain a hydrolase preparation that allows a lysis of said oleaginous microorganism's cell wall. In one embodiment, said inducing system is said residual biomass of said oleaginous microorganism produced during step e) and/or f), or is a part or component of said residual biomass.

In one embodiment, said hydrolase obtained from said fungus is prepared separately (from performing steps d)-f) of the present invention) and is used in step e) as a liquid preparation directly obtained from culturing said fungus, or as a freeze-dried preparation that is subsequently reconstituted in solution to be used in step e). In one embodiment, said hydrolase contains one or several activities for example, but not limited to enzyme activities selected from cellulase, xyloglucanase, beta-glucosidase, mannanase, xylanase, and laminarinase enzyme activities. In one embodiment, said protease, if present, is selected from proteases produced by *Aspergillus* sp., *Streptomyces* sp. or *Bacillus* sp. In one embodiment according to the present invention, the "purely enzymatic treatment" additionally involves the treatment of said microorganism with a protease (but still excludes a pretreatment, or solvent-based extraction or chemicals based demulsification). It should be noted that such protease, if and when used, follows or is combined with a treatment using the aforementioned hydrolase. Without wishing to be bound by any theory, the present inventors believe that the treatment involving a protease allows a separation of the produced lipids from any proteins associated therewith and therefore assists in the release of lipids. In one embodiment, the protease is selected from the group of proteases produced by *Aspergillus* sp., *Streptomyces* sp. or *Bacillus* sp.

In one embodiment, during step e), if present, the "purely enzymatic treatment of said cultivated second microorganism without any solvent-based extraction" is a treatment of said microorganism with a hydrolase. Preferably, such hydrolase is obtained from another microorganism, preferably from a fungus, more preferably from a filamentous fungus. In one embodiment, the fungus is selected from the Genus *Trichoderma, Aspergillus, Penicillium, Aureobasillium* and *Fusarium*. In a more preferred embodiment, the filamentous fungus is *Trichoderma reesei*, because this has proved to produce a particularly efficient hydrolase that allows a lysis of the cell wall of the oleaginous microorganism. In one embodiment, said hydrolase is obtained from a fungus, preferably a filamentous fungus that has been cultured in the presence of an inducing system, wherein, preferably, said inducing system is a component of said oleaginous microorganism, preferably one or several cell-wall components of said oleaginous microorganism used for producing microbial lipids, so as to obtain a hydrolase preparation that allows a lysis of said oleaginous microorganism's cell wall. In one embodiment, said inducing system is said residual biomass that may be produced during steps e) und f), or components thereof. Preferably, such hydrolase is produced by culturing said filamentous fungus in the presence of cell wall fragments of said oleaginous microorganism. Without wishing to be bound by any theory, the present inventors believe that exposure of the filamentous fungus, e.g. *T. reesei*, to the presence of such cell wall component of said oleaginous microorganism allows such filamentous fungus to produce exactly the suitable enzyme (s) to complete the lysis of the cell-walls of the oleaginous microorganism. In a particularly preferred embodiment, a filamentous fungus from the genus *Trichoderma* is used, e.g. *Trichoderma reesei*, and in a particularly preferred embodiment, a mutant of *Trichoderma reesei* is used, such as the mutant having the ATCC deposition number(s) 56765 and 13631. Once the filamentous fungus has been cultivated, the resultant culture may be further processed, such as concentrated, and the biomass of the fungus itself is removed, and the resultant supernatant may be used in such a form, or it may be freeze-dried and kept for storage and subsequent reconstitution in an appropriate aqueous solution. Again, without wishing to be bound by any theory, the present inventors believe that the hydrolase thus produced may represent a combination of various enzymatic activities, e.g. a cellulase, xyloglucanase, β-glucosidase, mannanase, xylanase and laminarinase, and, possibly, others.

In one embodiment, the term "amenable for subsequent harvesting", as used herein, relates to facilitating harvesting of microbial lipids, e.g. by making the produced microbial lipids accessible for a subsequent recovery such as accessible for a subsequent recovery from the culture vessel. For example, by performing a purely enzymatic treatment of the oleaginous microorganism, the microbial lipids become accessible for subsequent harvesting. In one embodiment, the terms "amenable" and "accessible" are used interchangeably.

In one embodiment, by performing a purely enzymatic treatment of the oleaginous microorganism without any solvent-based extraction or chemicals-based demulsification, the microbial lipids are made amenable for subsequent harvesting, e.g. by a density-based separation method. In one embodiment, said density-based separation method is selected from separation based on natural gravity, gravity-assisted phase separation, and centrifugation, wherein each of said separation based on natural gravity, gravity-assisted phase separation, and centrifugation, is performed alone or in combination with a decantation, aspiration or other mechanical harvesting method.

The growth of the oleaginous microorganism in a suitable medium comprising an enzymatically treated substrate, allows said oleaginous microorganism to produce microbial lipids. However, typically, these microbial lipids are still contained within the cells of the oleaginous microorganism and, for a subsequent recovery, therefore need to be made accessible. Embodiments of the present invention therefore provide for an enzymatic treatment of the grown oleaginous microorganism that makes the produced microbial lipids amenable or accessible to a subsequent recovery from the culture vessel. It should be noted that the method according to the present invention involves a purely enzymatic treatment of the grown oleaginous microorganism without having to rely on any pretreatment steps, e.g. chemical pretreatment steps, or subsequent or concomitant extraction of said lipids using a solvent. Examples of such chemical pretreatment steps or subsequent or concomitant extraction steps are solvent-based extraction or chemicals based demulsification. Such excluded pretreatment steps may, however, also be physical steps, such as temperature changes, pressure changes, centrifugation, sonification, irradiation, etc. The term "chemicals based demulsification", as used herein refers to the exposure of the grown biomass to a demulsifier so as to enable the breaking of any emulsion (that may have formed).

In accordance with embodiments of the invention, the method does not involve a solvent-based extraction, chemicals based demulsification or other treatments, such as temperature shock, chemical treatment or high-pressure homogenization or ultrasound homogenization. These would potentially add to the costs or the hazardous character of the method and are avoided by the present invention. The advantage of such absence of a solvent-based extraction and chemicals based demulsification is that the downstream products, particularly the microbial oil, is suitable for further processing into food stuff. Particularly, the microbial oil produced with a method of the invention can be directly used to prepare foodstuff, e.g. due to the absence of solvent and/or chemicals residues in the microbial oil. The present inventors have surprisingly found that such harsh treatment steps are not strictly necessary.

In embodiments according to the present invention, the produced microbial lipids are harvested using a density-based separation method. In its simplest form, such density-based separation method may be a process wherein the culture of the oleaginous microorganism is simply allowed to stand for a period of time as a result of which the lipid phase will separate from an aqueous phase due to different densities and/or solubility in water. This may be combined with a subsequent decantation, aspiration or other mechanical removal of the lipid-phase from the culture. In other embodiments, separation may occur by way of a gravity-assisted phase separation, by way of a centrifugation, alone or in combination with a subsequent mechanical removal or the lipid-phase, e.g. a decantation or aspiration.

In one embodiment, said method comprises said step e) of performing said purely enzymatic treatment of said cultivated second microorganism without any solvent-based extraction or chemicals-based demulsification, wherein said purely enzymatic treatment of said cultivated second microorganism is a treatment of said microorganism with a hydrolase, alone, or in combination with/followed by a protease. In one embodiment, steps d) and e) are performed within the same reaction vessel. This is herein also something referred to as a "one-pot-method" or "one-pot-process". In this embodiment, the method according to the present invention may be considered a one-pot process for the manufacture of microbial lipids, particularly food-grade microbial lipids.

In one embodiment, step e) and/or f) results in a lipid-phase, and a hydrolysate of said oleaginous microorganism. In some instances, step e) and/or f) may additionally also result in a residual biomass of said oleaginous microorganism which residual biomass is different from said lipid phase and said hydrolysate. In one embodiment, said method involves a repeated performance of steps d)-f), and wherein said hydrolysate of said oleaginous microorganism resulting from steps e) and/or f) is reused/recycled for performing step d). In such an embodiment, the microorganism hydrolysate resulting from steps e) and/or f) is re-fed into the medium used in step d) and may act as an additional carbon source (additional to a carbon source present in the enzymatically treated substrate). Embodiments, wherein, in steps d)-f) side products are reused/recycled, e.g. wherein products resulting from steps e) and/or f) are reused/recycled in step d), avoid the occurrence of waste-products. Such embodiments may therefore herein also sometimes be referred to as a "waste-free process" or "waste-free method". In one embodiment, steps d)-f) are performed 2-times to n-times, wherein n is an integer, selected from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In one embodiment, steps d)-f) are performed 2-3 times. A repeated recycling allows to make efficient use of the various media involved and avoids the production of excessive waste, since the products resulting from the process, such as a hydrolysate of the oleaginous microorganism, is reused as a starting medium to grow such oleaginous microorganism.

In one embodiment, the method of the invention further comprises one or more steps of harvesting said protein biomass and/or said aroma compounds, e.g. using any of centrifugation, filtration, distillation, organophilic pervaporation, solid-phase micro extraction, sedimentation, coagulation, floating, and combinations thereof, preferably using any of centrifugation, filtration, distillation, organophilic pervaporation, solid-phase micro extraction, and combinations thereof. In one embodiment, the method of the invention is performed in fed-batch, semi-continuous or continuous mode, wherein optionally, said method involves the repeated addition of an organic acid.

In one embodiment, the method of the invention comprises a step of pretreating said first substrate and/or, if step c) is present, pretreating said second substrate, by

- mechanical pretreatment, preferably by milling, mixing, shredding, and/or sieving said substrate(s);
- dissolving said substrate(s) in a dissolvent, preferably in water;
- chemical hydrolysis of said substrate(s), preferably using an acid, e.g. sulfuric acid; e.g. using an acid, preferably sulfuric acid, at a concentration in the range from 0.1-10 vol % at a temperature in the range from 20-260° C., preferably 80 to 140° C., for a duration of from 1 sec to 24 h, preferably 30 min to 3 h;
- thermal pretreatment of said substrate(s), preferably at a temperature of from 50° C. to 200° C. for 10 min to 240 min, more preferably at a temperature of from 80° C. to 170° C. for 30 min to 90 min;
- fermentative pretreatment of said substrate(s), preferably an anaerobic fermentation; and/or
- enzymatic pretreatment of said substrate(s) using one or more enzymes, optionally commercially available enzymes; wherein said one or more enzymes are selected from proteases, e.g. endo- and exo-peptidases, serine endopeptidase, subtilisin A, and pepsin; and hydrolases, preferably glycoside hydrolases, more preferably glycoside hydrolases selected from α-amylases, amyloglucosidases, cellulases, hemicellulases, xylanases, xyloglucase, galactanase, arabinase, mannanase, lipase, glucoamylases, and pectinases.

In one embodiment, said first and/or second substrate is pretreated using a combination of any of said mechanical pretreatment, said dissolving, said chemical hydrolysis, said thermal pretreatment, said fermentative pretreatment, and said enzymatic pretreatment. In one embodiment, such step of pretreating said first substrate, if present, is performed prior to cultivating said first microorganism with the first substrate. In one embodiment, said step of pretreating said second substrate using any of said mechanical pretreatment, said dissolving, said chemical hydrolysis, said thermal pretreatment, said fermentative pretreatment, said enzymatic pretreatment, or any combination thereof, is a further pretreatment in addition to said pretreating a second substrate with said at least one enzyme of step c). For example, said step of pretreating said second substrate using any of said mechanical pretreatment, said dissolving, said chemical hydrolysis, said thermal pretreatment, said fermentative pretreatment, said enzymatic pretreatment, or any combination thereof, is performed prior to and/or subsequent to said pretreating a second substrate with said at least one enzyme of step c). In one embodiment, such step of pretreating said second substrate, if present, is performed prior to cultivating said second microorganism with the second substrate, preferably prior to pretreating the second substrate with said at least one enzyme of step c). In one embodiment, said fermentative pretreatment is an anaerobic fermentation using an anaerobic microorganism. In one embodiment, said fermentative pretreatment comprises a treatment of said substrate at a pH in the range of from pH 2.5 to pH 5.5, preferably pH 3 to pH 4, at a temperature in the range of from 20° C. to 50° C., preferably 25° C. to 40° C., at a $pO_2$ in the range of from 0-30%, preferably 5-10%, for 1-5 days, preferably 1-3 days, and/or at an agitation of from 50 rpm to 500 rpm.

In one embodiment, said pretreating said first substrate and/or second substrate is an enzymatic pretreatment which is a hydrolysis. In one embodiment, said step of pretreating said first substrate and/or said second substrate comprises an enzymatic pretreatment which is a hydrolysis. A hydrolysis, e.g. of starch contained in said food residue(s), may comprise two stages; in the first stage, α-amylase is used to liquefy the starch, thereby providing a solution including dextrins and glucose; in the second stage, the liquefied starch is subjected to glucoamylase. In one embodiment, said step of pretreating said first substrate and/or said second substrate comprises an enzymatic pretreatment comprising a treatment with α-amylase and glucoamylase. In one embodiment, the method of the invention comprises a step of refining the microbial lipids harvested in step f), e.g. by physical refining.

In one embodiment, the capacity of the first or second microorganism to produce enzymes, protein biomass, microbial lipis, and/or aroma compounds is further improved by genetic modification, e.g. by untargeted or targeted genetic alteration. In one embodiment, said untargeted genetic alteration comprises chemical- or radiation-induced mutation. In one embodiment, said radiation-induced mutation comprises any of UV, ionizing, gamma rays, X-rays, and neutron radiation. In one embodiment, said targeted genetic alteration comprises CRISPR-CAS systems, bacterial transformation, and/or plasmid-based insertion.

In one embodiment, the method of the invention is a method of producing microbial lipids and preparing foodstuff therewith, wherein said method comprises a step, e.g. step g), of preparing a foodstuff comprising the microbial lipid harvested in step f), preferably a bakery product, e.g. bread, bread roll, biscuit, muffin, cookie, or cake; a confectionery product, e.g. flour confectionary or sugar confectionary; a dairy product, e.g. ice cream or baby milk; a spread, e.g. margarine, mayonnaise, or soft cheese; a convenience food, e.g. instant noodles, pizza, pizza dough, or sauce; a beverage; vegetarian or vegan food, e.g. meat analogues and milk analogues; sweets, e.g. cocoa-free chocolate; and/or a chocolate product; wherein, optionally, said method further comprises a step, e.g. step h), of recycling a food residue(s) of said foodstuff by using said food residue(s) of said foodstuff as said first substrate and/or, if step c) is present, as said second substrate. In one embodiment, the method is a method for recirculation of food residues, i.e. food residue(s) is converted into food-grade products, e.g. microbial oil, protein biomass, and/or aroma compounds, which are further processed into foodstuff. Residue(s) of such foodstuff, e.g. food residues, can subsequently be converted into food-grade products using the method of the invention. Advantageously, the method of the invention increases the efficiency of the food chain and the use of food resources. An advantage of the method and use of the invention is that food residue(s) and/or food loss is/are decreased by converting such food residue(s) into edible raw materials, such as microbial oil and optionally protein biomass and/or aroma compounds. In one embodiment, when referring to preparing foodstuff "therewith" or "there from" in the context of a product such as microbial lipid, it is meant that foodstuff is prepared which comprises said product.

An advantage of the method of the invention is that the microbial food ingredients produced, particularly microbial lipids and protein biomass and/or aroma compounds, allow to produce foodstuff comprising said microbial food ingredients, since the microbial food ingredients are food-grade ingredients. For example, the microbial lipids produced by bread residue hydrolysate fermentation can replace palm oil in baking applications, such as bread, praline production, ice cream, instant noodles, margarine, chocolate, pizza dough and cookie production. Aroma compounds can be used to flavor foods according to Commission Implementing Regulation (EU) No 872/2012, preferably dairy products, and confectionery products. The protein biomass produced with a method of the invention, preferably as a side product of the method of producing microbial lipids, can be used as a meat alternative for any minced or formed meat application like burger patties, chili, nuggets, meat sauce and sausages. In one embodiment, the food-grade properties of the involved components are ensured during the whole process of a method of the invention. Thus, a method of the invention allows to achieve a sustainable use of food resources and reduces food waste and food loss. Particularly, the method of the invention unexpectedly allows to use food residue(s), preferably food-grade food residue(s) to produce a valuable raw material such as microbial lipids, protein biomass, and/or aroma compounds, which subsequently can be used to produce food; residue(s) from such produced food in turn can be recycled and used as a substrate in a method of the invention to produce further food. Conclusively, advantageously, the method of the invention can be used as a cycle.

A further advantage of the method of the invention is that the method does not need a cultivation of the oleaginous microorganism in a two-step process, wherein a first step is under non-limiting conditions for biomass formation and a second step is under new trend-limiting conditions for lipid production induction. Instead, the method of the invention allows for a cultivation in which lipid is directly accumulated. Particularly, by providing a medium comprising said enzymatically treated first substrate and/or said enzymatically treated second substrate to said second microorganism in step d), a high accumulation of intracellular lipids is achieved. Particularly, by providing said medium to said second microorganism, high protein biomass and lipid yields are achieved. For example, a lipid yield of 84.9% of the dry cellular weight was achieved. Furthermore, a protein biomass yield of up to 60% of the dry fungal biomass was achieved. Advantageously, a step of nutrient restriction is not needed to prepare microbial oil with said oleaginous microorganism. An even further advantage of the method of the invention is that only a mild downstream processing is needed, for example a purely enzymatic treatment can be performed to make the microbial lipids amenable for subsequent harvesting, and thus no hazardous chemicals are involved; the harvested microbial lipids thus do not comprise hazardous residues and are edible.

In one embodiment, the term "use of a microbial lipid in the production of a foodstuff", as used herein, relates to producing foodstuff comprising a microbial lipid, preferably the microbial lipid obtained with the method according to the present invention. In one embodiment, the use of a microbial lipid in the production of a foodstuff comprises replacing fat(s) in a recipe of a foodstuff by said microbial lipid. For example, microbial lipid can replace fats such as palm oil in foods, e.g. bakery products. In one embodiment, the use of a microbial lipid in the production of a foodstuff further comprises using protein biomass and/or aroma compounds, preferably protein biomass and/or aroma compounds obtained with a method of the invention, in the production of said foodstuff. For example, food may be provided which comprises said microbial lipid and said protein biomass and/or aroma compound. In one embodiment, the terms "foodstuff", "food product", and "food" are used interchangeably. In one embodiment, the use of the invention comprises a method of producing microbial lipids and preparing foodstuff therefrom, as defined herein. In one embodiment, the use of the invention comprises using a microbial lipid produced using a method for producing microbial lipids as defined herein in the production of a foodstuff.

In one embodiment, the term "composition comprising at least five, preferably at least six, more preferably at least seven enzymes", as used herein, relates to an enzyme mix. In one embodiment, said composition is obtainable performing step b) of a method of the invention. In one embodiment, step b) of a method of the invention results in the production of said composition by said first microorganism. In one embodiment, the composition is tailored to said first substrate. In one embodiment, the composition comprises enzymes selected from cellulase; lichenase; xylanase; arabinanase; amylase, e.g. α-amylase; limit dextrinase; pullulanase; protease; galactanase; mannanase; rhamnogalacturonan hydrolase; rhamnogalacturonan lyase; xyloglucanase; hemicellulase; amyloglucosidase; beta-glucosidase; pectinase; and laminarinase. In a preferred embodiment, the composition comprises enzymes selected from cellulase; lichenase; xylanase; arabinanase; amylase, e.g. α-amylase; limit dextrinase; pullulanase; protease; galactanase; mannanase; rhamnogalacturonan hydrolase; and rhamnogalacturonan lyase. In one embodiment, the composition comprises enzymes selected from cellulase; lichenase; xylanase; arabinanase; amylase, e.g. α-amylase; limit dextrinase; pullulanase; protease; galactanase; and mannanase; or selected from cellulase; xylanase; arabinanase; amylase, e.g. α-amylase; limit dextrinase; pullulanase; galactanase; mannanase; rhamnogalacturonan hydrolase; and rhamnogalacturonan lyase. In a preferred embodiment, the composition, e.g. a composition produced in step b) of the method of the invention using bread residue as a first substrate, comprises enzymes selected from cellulase; amylase; hemicellulase; limit dextrinase e.g. malt limit dextrinase; and pectinase. In one embodiment, the composition of the invention comprises or consists of cellulase; amylase; hemicellulase; limit dextrinase e.g. malt limit dextrinase; and pectinase. In one embodiment, said composition is a food-grade composition.

In one embodiment, said composition is produced in step b) of the method for producing microbial lipids as defined herein, wherein, preferably, said composition comprises or consists of said at least one enzyme produced in step b) of the method for producing microbial lipids as defined herein.

In one embodiment, said composition is producible in step b) of the method for producing microbial lipids as defined herein, wherein, preferably, said composition comprises or consists of said at least one enzyme producible in step b) of the method for producing microbial lipids as defined herein. In one embodiment, said at least one enzyme produced in step b) of the method for producing microbial lipids as defined herein comprises or consists of the composition of the invention. In one embodiment, said composition is a food-grade composition, if said first substrate in step b) of the method for producing microbial lipids is a food-grade food residue(s).

In one embodiment, said composition is obtained in step c) of the method for producing microbial lipids as defined herein, wherein, preferably, said composition comprises or consists of said at least one enzyme obtained in step c) of the method for producing microbial lipids as defined herein. In one embodiment, said composition is obtainable in step c) of the method for producing microbial lipids as defined herein, wherein, preferably, said composition comprises or consists of said at least one enzyme obtainable in step c) of the method for producing microbial lipids as defined herein. In one embodiment, said at least one enzyme obtained in step c) of the method for producing microbial lipids as defined herein comprises or consists of the composition of the invention. In one embodiment, said at least one enzyme obtained in step c) of the method for producing microbial lipids as defined herein is the composition of the invention. In one embodiment, the composition of the invention is a by-product of a method for producing microbial lipids as defined herein.

In one embodiment, said cultivating a second microorganism of step d) is performed at a temperature in the range of from 18° C. to 37° C., preferably 18° C. to 33° C. In one embodiment, said cultivating a second microorganism of step d) is performed at a pH in the range of from pH 3 to pH 9. In one embodiment, said cultivating a second microorganism of step d) is performed for 1 to 12 days, preferably for 3 to 10 days. In one embodiment, said cultivating a second microorganism of step d) is performed with pO2>20%. In one embodiment, said cultivating a second microorganism of step d) is performed under agitation, preferably under stirring with a rotational speed in the range of from 50 to 800 rpm. In one embodiment, said cultivating a second microorganism of step d) is performed at a temperature in the range of from 10° C. to 37° C., preferably 18° C. to 33° C., at a pH in the range of from pH 3 to pH 9, for 1 to 12 days, preferably for 2 to 10 days, with pO2>20%, under agitation, preferably under stirring with a rotational speed in the range of from 50 to 800 rpm. In one embodiment, said cultivating a second microorganism of step d) comprises cultivating said second microorganism for 2 to 12 days, preferably for 3 to 10 days, at a temperature in the range of from 18° C. to 37° C., preferably 18° C. to 33° C., at a pH in the range of from pH 3 to pH 8, and/or at a dissolved oxygen (pO2) pO2>30%.

In one embodiment, the method is particularly suitable for producing lipids with a content of >60% unsaturated fatty acids with respect to the total fatty acids content and/or a pour point in a range of <10° C., e.g. from 9° C. to 5° C., such as for example approximately 5° C. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 10-20° C., dissolved oxygen content 10-30% and/or addition of crotonic acid (e.g. 0-10% of total organic acid), and thereby allowing said oleaginous microorganism to produce microbial lipids, which are characterized by a "pour point" in a range of <10° C., e.g. from 9° C. to 5° C., such as for example ca. 5° C., and/or an unsaturated fatty acid content of >60% with respect to the total fatty acid content. The "pour point", as used herein, is typically determined in accordance with any of the following standards: DIN51597, DIN EN 23015:1994-05, DIN ISO 3015:1982-10, DIN ISO 3016:1982-10, ASTM D97, ASTM D5985, preferably using DIN ISO 3016.

In one embodiment, the method is suitable for producing lipids with a content of 20-65% saturated fatty acids with respect to the total fatty acids content and/or a triglycerides POP C18:1-C16:0), POS (C16:0-C18:1-C18:0), and SOS (C18:0-C18:1-C18:0) content of 40-85% with respect to the total triglycerides content. In one embodiment, the method is suitable for producing lipids that equivalent to cocoa-butter-like microbial-oil. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 20-33° C., dissolved oxygen content 10-30%, pH 5-8, and/or addition of butyric acid and propionic acid (e.g. 1-60% of total organic acid); optionally further comprising a genetic modification of a fatty acid synthase, delta 9 desaturase, and/or delta 12 desaturase; and thereby allowing said oleaginous microorganism to produce microbial lipids, which are characterized by high content of triglycerides POP, POS, and SOS content of 40-85% with respect to the total triglycerides content.

In one embodiment, the method is suitable for producing lipids with a content of 20-55% saturated fatty acids with respect to the total fatty acids content and/or a triglycerides PPP, PPS, PSS, and SSS content of 1-20% with respect to the total triglycerides content. In one embodiment, the method is suitable for producing lipids that equivalent to palm-stearin-like microbial-oil and/or palm-like microbial-oil. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 22-33° C., dissolved oxygen content >10-40%, pH 5-8, addition of butyric acid and propionic acid (e.g. 1-50% of total organic acid); optionally further comprising a genetic modification of any of a fatty acid synthase, delta 9 desaturase, and/or delta 12 desaturase; and thereby allowing said oleaginous microorganism to produce microbial lipids, which are characterized by content of triglycerides PPP, PPS, PSS, and SSS content of 1-20% with respect to the total triglycerides content.

In one embodiment, the method is suitable for producing lipids with a content of 20-55% saturated fatty acids with respect to the total fatty acids content and/or a fatty acid C10, C12, and/or C14 content of 1-60% with respect to the total triglycerides content. In one embodiment, the method is suitable for producing lipids that equivalent to palm-kernel-oil-like microbial-oil. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 25-30° C., dissolved oxygen content >30%, pH 6-8; optionally further comprising a genetic modification of any of a fatty acid synthase, thioesterases, delta 9 desaturase, and/or delta 12 desaturase; and thereby allowing said oleaginous microorganism to produce microbial lipids, which are characterized by content of triglycerides PPP, PPS, PSS, and SSS content of 1-20% with respect to the total triglycerides content.

In one embodiment, the method is suitable for producing lipids with a content of 10-45% poly unsaturated fatty acids with respect to the total fatty acids content and/or a fatty acid content of α-linolenic acid (ALA), eicosapentaenoic acid (EPA), and/or docosapentaenoic acid (DPA) of 10-45% with respect to the total fatty acids content. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 15-28° C., dissolved oxygen content >40%, pH 6-8; optionally further comprising a genetic modification any of a fatty acid synthase, thioesterases, delta 4, 5, 6, 8, 9, 12, and/or 15 desaturases, and/or delta 5, 6, and/or 9 elongases; and thereby allowing said oleaginous microorganism to produce microbial lipids, which are characterized by a fatty acid content of α-linolenic acid (ALA), eicosapentaenoic acid (EPA), and/or docosapentaenoic acid (DPA) of 10-45% with respect to the total fatty acids content.

In one embodiment, the method is particularly suitable for producing lipids with a content of >50% unsaturated fatty acids with respect to the total fatty acids content and/or a triglycerides POO, OOS, and 000 content of 50% with respect to the total triglycerides content. In one embodiment, the method is suitable for producing lipids that equivalent to palm-olein-oil-like microbial-oil, sunflower-oil-like microbial-oil, rapeseed-oil-like microbial-oil. This is particularly so, if the following parameters are chosen for step d):

growing said oleaginous microorganism in a medium comprising an enzymatically treated substrate, e.g. an enzymatically treated first substrate and/or an enzymatically treated second substrate, under the following conditions: temperature 10-30° C., dissolved oxygen content 10-30% and/or an addition of crotonic acid (e.g. 0-10% of total organic acid), and thereby allowing said oleaginous microorganism to produce microbial lipids, which are characterized by a "pour point" in a range of <10° C., e.g. from 9° C. to 5° C., such as for example ca. 5° C., and/or an unsaturated fatty acid content of >60% with respect to the total fatty acid content.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

BRIEF DESCRIPTION OF THE SEVERAL VIEWS OF THE DRAWINGS

The present invention is now further described by reference to the following figures.

All methods mentioned in the figure descriptions below were carried out as described in detail in the examples.

Figure 1:
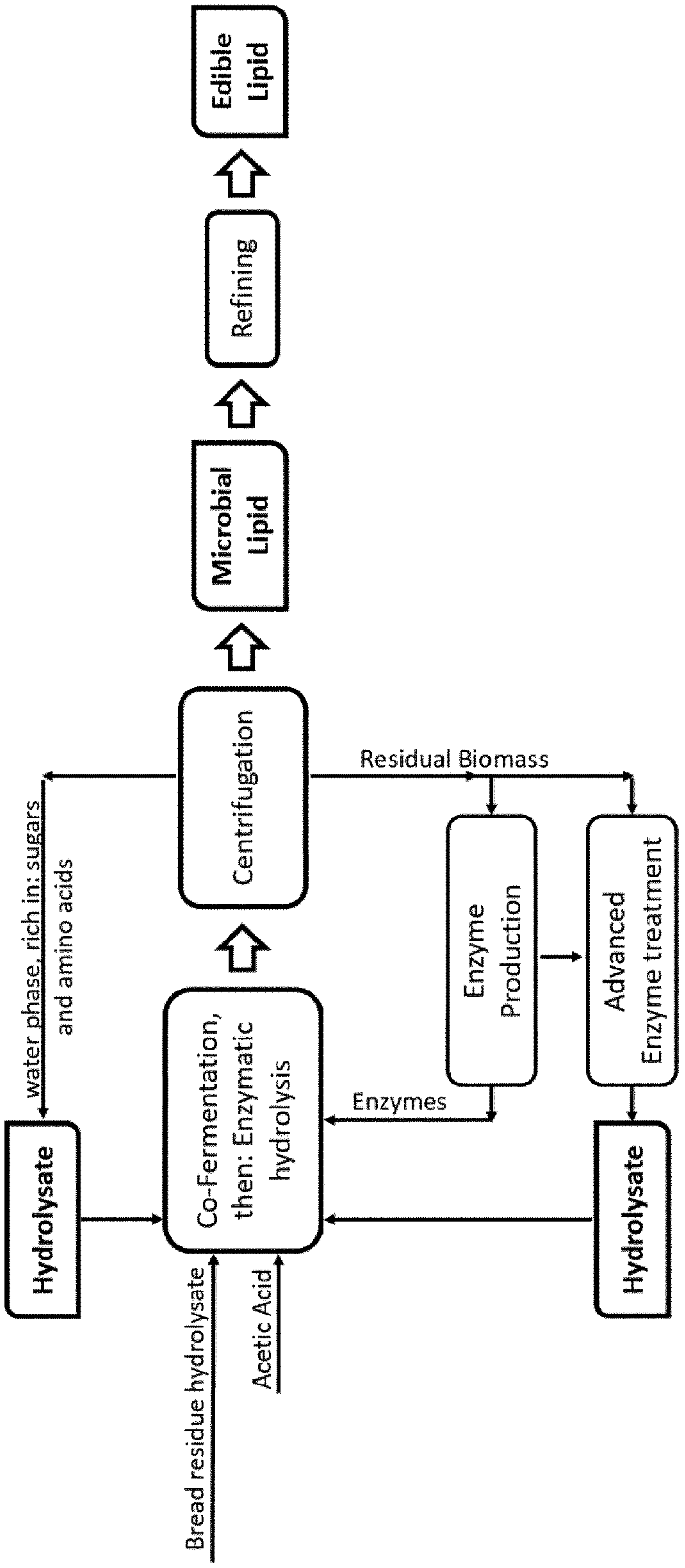
FIG. 1 shows a schematic flowchart of the method of the invention which is a sustainable method for producing edible microbial lipids.
Figure 2:
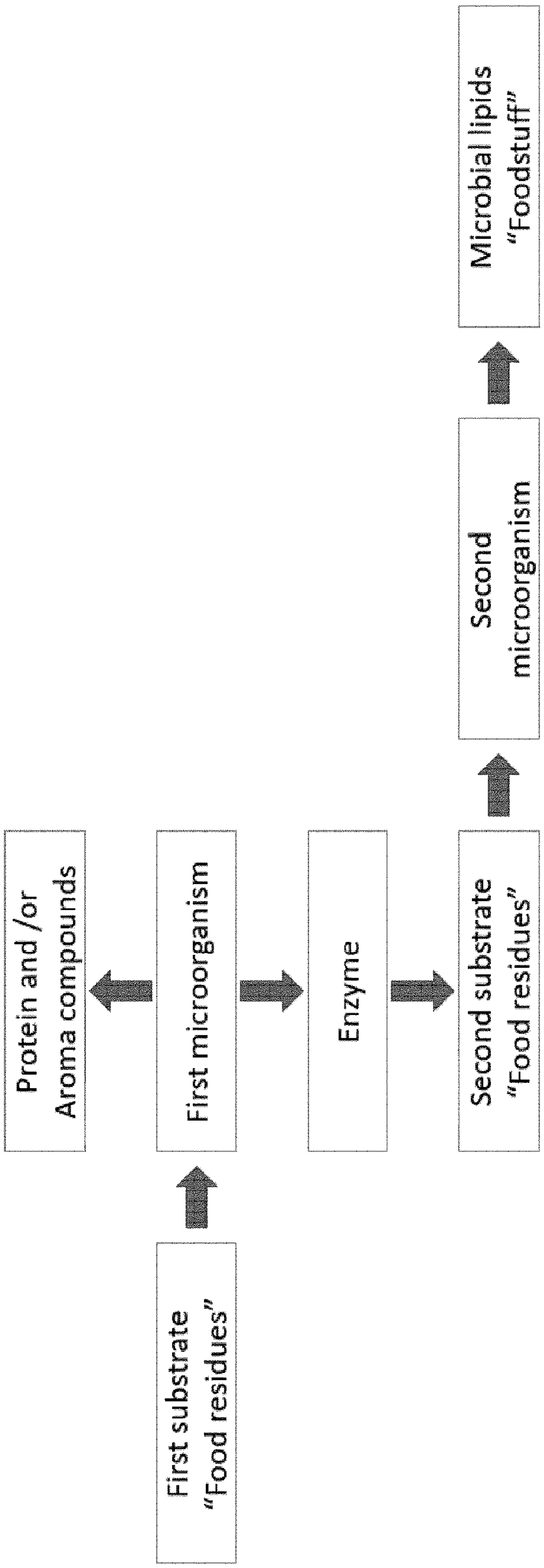
FIG. 2 shows a flow diagram of a method of the invention. A first substrate, particularly food residue(s) is used as a substrate for a first microorganism. The first microorganism produces an enzyme mix to digest said first substrate (said enzyme mix producing an enzymatically treated first substrate), and optionally further produces protein biomass and/or aroma compounds. Optionally, the first microorganism can be co-cultivated with microalgae which produce enzyme(s), proteins, and/or aroma compounds. The enzymatically treated first substrate can be used as or in a growth medium for cultivating a second microorganism which produces microbial oil. Alternatively or additionally, the enzyme mix is used to enzymatically treat a second substrate, which is preferably of the same type as the first substrate, thereby obtaining an enzymatically treated second substrate which can be used as or in a growth medium for cultivating a second microorganism which produces microbial oil. The enzymatically treated first substrate and the enzymatically treated second substrate can also be combined to provide a growth medium for said second microorganism.
Figure 3:
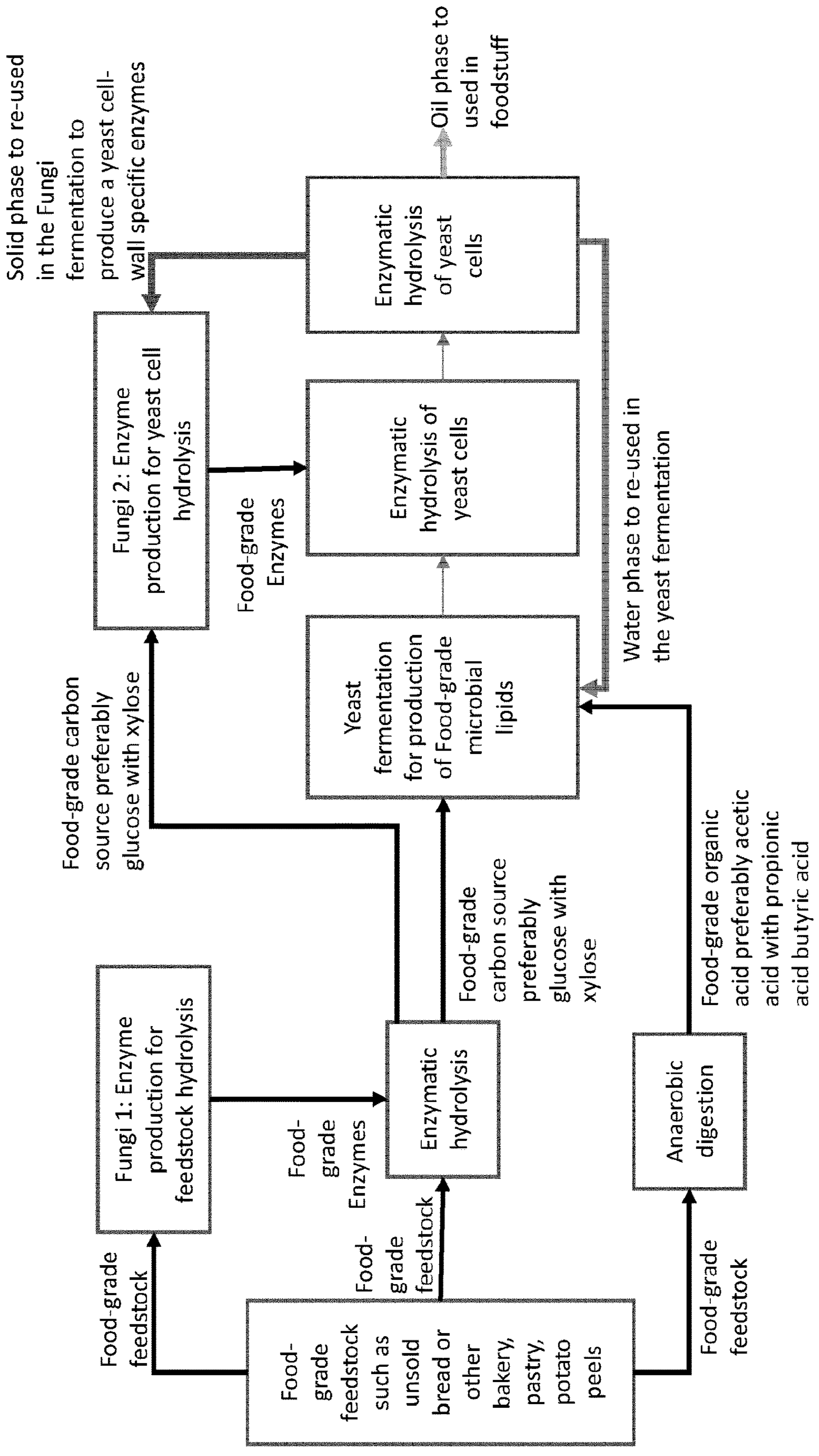
FIG. 3 shows a flow diagram of an embodiment of the method of the invention.
Figure 4:
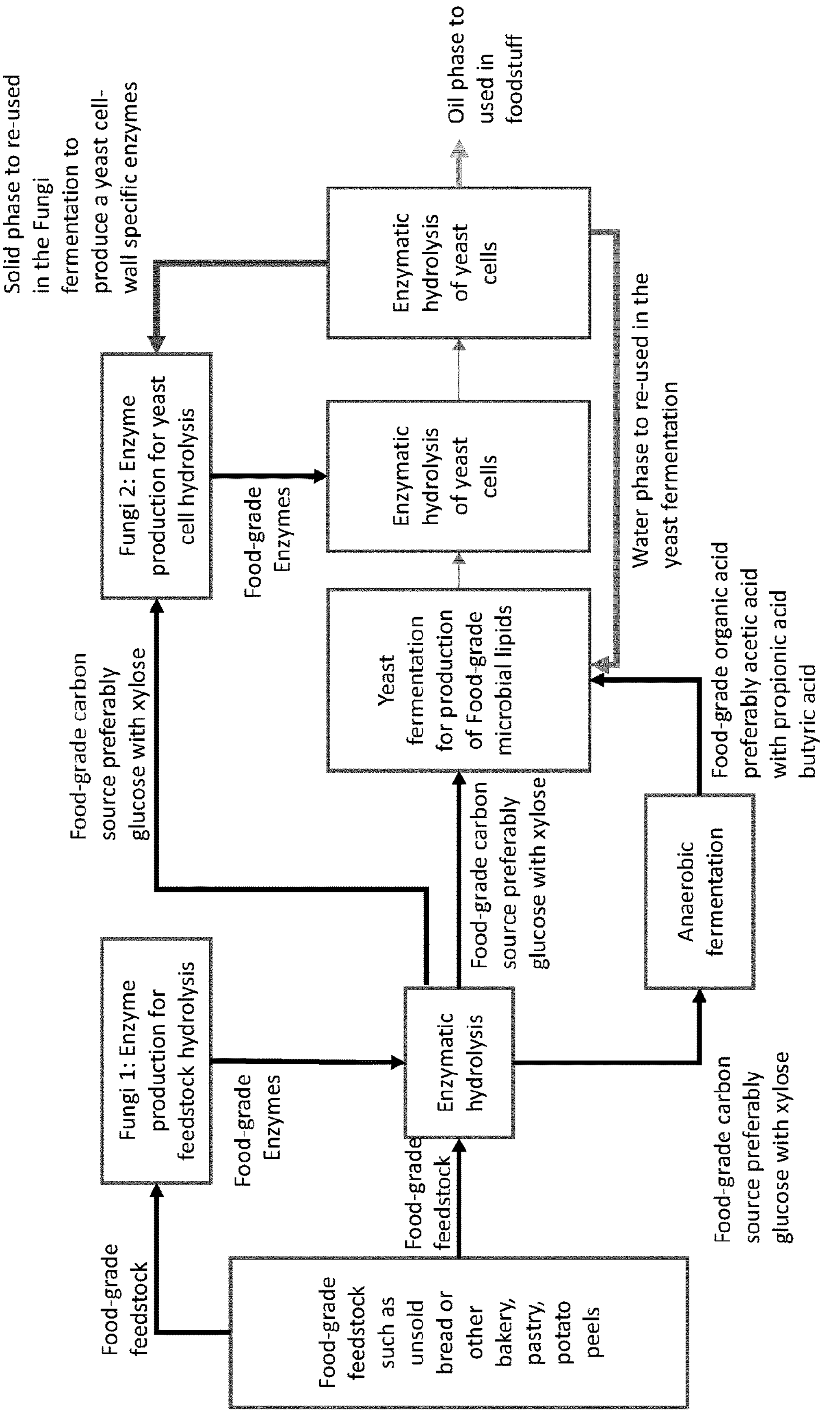
FIG. 4 shows a flow diagram of an embodiment of the method of the invention.
Figure 5:
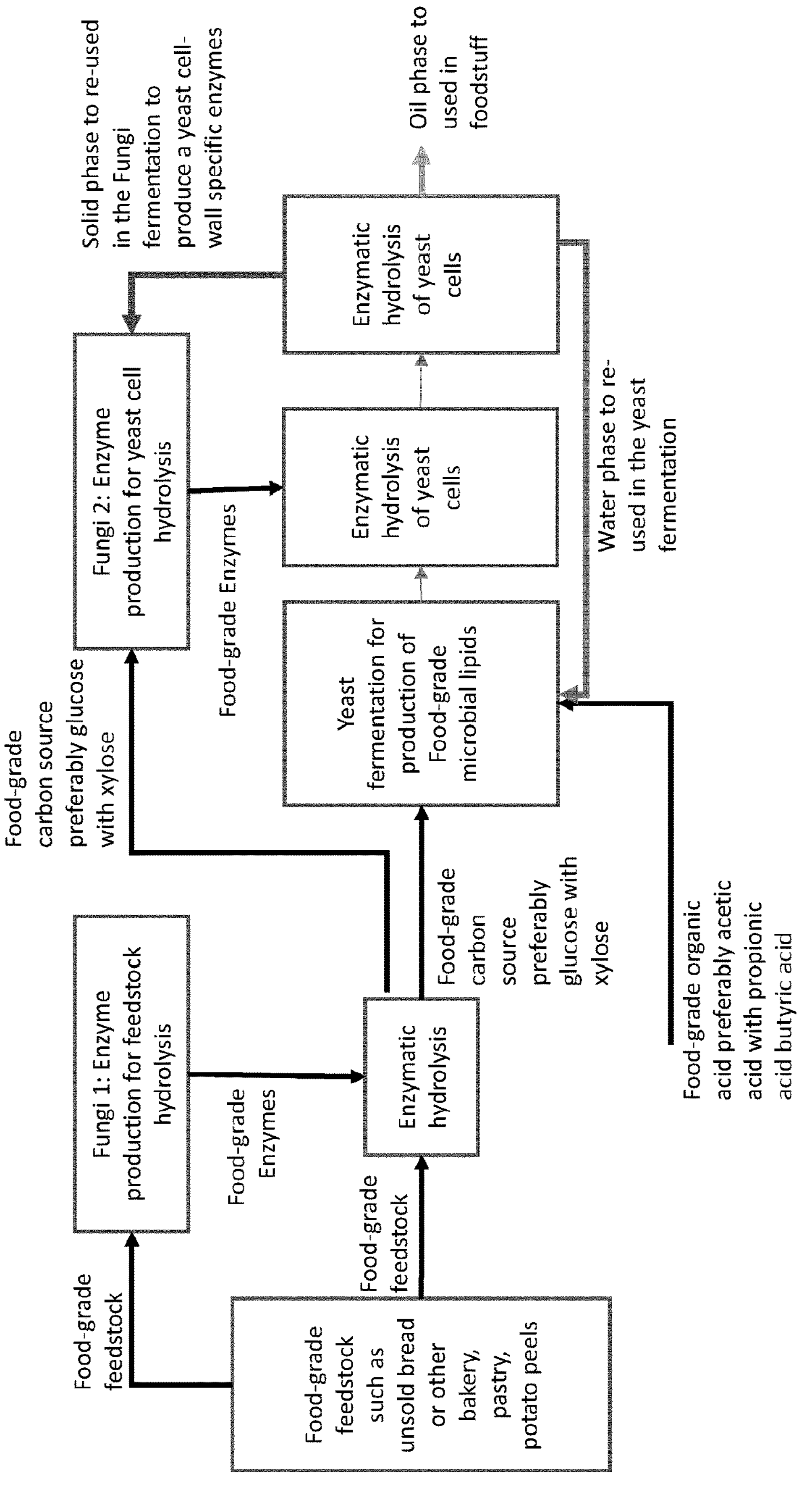
FIG. 5 shows a flow diagram of an embodiment of the method of the invention.

In the following, reference is made to the examples, which are given to illustrate, not to limit the present invention.

EXAMPLES

Example 1: Raw Material Selection and Composition Analysis-Bread Residue

An exemplary food residue(s) that can be used as first substrate and/or substrate used in a method for producing microbial lipids of the invention is bakery product food residue(s), such as bread residue. Today residual bread is commonly used in industry to get bread meal by grinding for bread production or as animal feed. Alternatively, the following example describes an exemplary process for selection of bakery supplied bread residues as feed stock for microbial fermentation and the composition analysis of this raw material. Fresh bread residues are collected and handled so as to avoid biological degradation and keep the food grade, which includes the steps of frequent residue pickup (e.g., at the same day after the residues determined unsaleable), drying fine sliced bread in a baking oven (e.g. starting temperature 160° C. without further heating overnight) and subsequently grinding to 4 mm particles with a stale bread mill. These bread crumbs are stored at room temperature for up to 2 weeks or frozen at −20° C. for up to 3 months. Bread residues are highly suitable as a substrate to be used in a method for producing microbial lipids of the invention, because bread residues are rich in nutrients, such as proteins, carbohydrates, fats, minerals, and vitamins (cf. Tables 1 and 2).

Table 1 shows an exemplary average nutrition value of wheat mixed bread [1]; Ingredients: wheat flour 54%, water, natural sourdough 12% (rye flour, water), rye flour, salt, rapeseed oil, yeast, acidity regulator sodium acetate.

| nutritional value | per 100 g (range) |
|---|---|
| Total lipid (fat) | 2.0 g (0.1-10.0 g) |
| thereof saturated fatty acids | 0.6 g (0.1-3.0 g) |
| Carbohydrates | 43.0 g (30.0-80.0 g) |
| thereof sµgars | 2.5 g (0.1-10.0 g) |
| Protein | 7.5 g (1.0-20.0 g) |
| Salt | 1.38 g (0.1-2.0 g) |
| Fibres | 4.0 g (0.1-10.0 g) |

Table 2 shows data of a composition analysis of wheat and rye bread in detail [2,3].

| nutritional value | per 100 g bread, wheat (range) | per 100 g bread, rye (range) |
|---|---|---|
| Protein | 10.7 g (1.0-20.0 g) | 8.5 g (1.0-20.0 g) |
| Total lipid (fat) | 4.5 g (0.1-10.0 g) | 3.3 g (0.1-10.0 g) |
| Carbohydrate. by difference | 47.5 g (30.0-80.0 g) | 48.3 g (30.0-80.0 g) |
| Fiber. total dietary | 4.0 g (0.1-10.0 g) | 5.8 g (0.1-10.0 g) |
| Sugars. total | 5.73 g (0.1-10.0 g) | 3.85 g (0.1-10.0 g) |
| Starch | 36.34 g (30.0-79.0 g) | n/a (30.0-79.0 g) |
| | Minerals | |
| Calcium | 125 mg (1-200 mg) | 73 mg (0.1-200 mg) |
| Iron | 3.6 mg (0.1-10 mg) | 2.8 mg (0.1-10 mg) |
| Magnesium | 41 mg (1-100 mg) | 40 mg (1-100 mg) |
| Phosphorus | 129 mg (1-200 mg) | 125 mg (1-200 mg) |
| Potassium | 141 mg (1-200 mg) | 166 mg (1-200 mg) |
| Sodium | 473 mg (100-1000 mg) | 603 mg (100-1000 mg) |
| Zinc | 1.04 mg (0.1-10 mg) | 1.14 mg (0.1-10 mg) |
| Copper | 0.148 mg (0.01-1 mg) | 0.168 mg (0.01-1 mg) |
| Manganese | 1.026 mg (0.1-10 mg) | 0.824 mg (0.1-10 mg) |
| Selenium | 28.8 µg (1-100 µg) | 30.9 µg (1-100 µg) |
| | Vitamins | |
| Vitamin C | 0.2 mg (0.01-2 mg) | 0.4 mg (0.01-2 mg) |
| Thiamine (B1) | 0.411 mg (0.01-2 mg) | 0.434 mg (0.01-2 mg) |
| Riboflavin (B2) | 0.252 mg (0.01-2 mg) | 0.335 mg (0.01-2 mg) |
| Niacin (B3) | 5.59 mg (0.1-10 mg) | 3.81 mg (0.1-10 mg) |
| Pantothenic acid (B5) | 0.82 mg (0.01-2 mg) | 0.44 mg (0.01-2 mg) |
| Vitamin B6 | 0.111 mg (0.01-2 mg) | 0.075 mg (0.01-2 mg) |
| Folate (B9) | 85 µg (10-200 µg) | 110 µg (10-200 µg) |
| Choline | 18.7 mg (1-100 mg) | 14.6 mg (1-100 mg) |
| Vitamin E (alpha-tocopherol) | 0.19 mg (0.01-2 mg) | 0.33 mg (0.01-2 mg) |
| Vitamin K (phylloquinone) | 4.9 µg (1-10 µg) | 1.2 µg (1-10 µg) |
| | Fatty acids | |
| Fatty acids. total saturated | 0.697 g (0.1-2 g) | 0.626 g (0.1-2 g) |
| Fatty acids. total monounsaturated | 0.612 g (0.1-2 g) | 1.311 g (0.1-2 g) |
| Fatty acids. total polyunsaturated | 1.615 g (0.1-10 g) | 0.799 g (0.1-10 g) |
| | Amino acids | |
| Tryptophan | n/a (0.01 g-1 g) | 0.096 g (0.01 g-1 g) |
| Threonine | n/a (0.01 g-1 g) | 0.255 g (0.01 g-1 g) |
| Isoleucine | n/a (0.01 g-1 g) | 0.319 g (0.01 g-1 g) |
| Leucine | n/a (0.01 g-1 g) | 0.579 g (0.01 g-1 g) |
| Lysine | n/a (0.01 g-1 g) | 0.233 g (0.01 g-1 g) |
| Methionine | n/a (0.01 g-1 g) | 0.139 g (0.01 g-1 g) |
| Cystine | n/a (0.01 g-1 g) | 0.173 g (0.01 g-1 g) |
| Phenylalanine | n/a (0.01 g-1 g) | 0.411 g (0.01 g-1 g) |
| Tyrosine | n/a (0.01 g-1 g) | 0.213 g (0.01 g-1 g) |
| Valine | n/a (0.01 g-1 g) | 0.379 g (0.01 g-1 g) |
| Arginine | n/a (0.01 g-1 g) | 0.325 g (0.01 g-1 g) |
| Histidine | n/a (0.01 g-1 g) | 0.182 g (0.01 g-1 g) |
| Alanine | n/a (0.01 g-1 g) | 0.299 g (0.01 g-1 g) |
| Aspartic acid | n/a (0.01 g-1 g) | 0.442 g (0.01 g-1 g) |
| Glutamic acid | n/a (0.1 g-10 g) | 2.603 g (0.1 g-10 g) |
| Glycine | n/a (0.01 g-1 g) | 0.302 g (0.01 g-1 g) |
| Proline | n/a (0.1 g-10 g) | 0.909 g (0.1 g-10 g) |
| Serine | n/a (0.01 g-1 g) | 0.417 g (0.01 g-1 g) |

Example 2: Production of Enzyme Solutions Via Cultivation of Fungi with Bread Residues as an Inducing System—*Aspergillus*

In this experiment the present inventors studied the production of an exemplary enzyme mix, e.g. enzyme solution, via submerged fermentation with *Aspergillus niger* van Tiegheim ATCC 10535 and bread residues as single media component. Therefore, appr. 100 g bread crumbs obtained as described before in example 1 where mixed with $ddH_2O$ to a total volume of 2 L (5% w/v) in a 5 L baffled Erlenmeyer flask in duplicate. After subsequent sterilisation by autoclaving at 121° C. for 20 min, the inoculum (spore suspension of *Aspergillus niger* van Tiegheim ATCC 10535) was added. The culture was incubated in a rotary shaker at 100 rpm at 28° C. Daily visual checks indicated good growth and enzymatic hydrolysis of the substrate because media was blacked by the fungi cells and liquefacting of bread crumbs was observed. The fermentation continued 3 weeks to stress the fungi and induce maximal hydrolase enzyme secretion. Filtration of the liquid culture with paper filter was applied to remove the vegetative cells subsequently. Spores were removed by centrifugation with a maximum of 75.600×g (Beckman Coulter Avanti JXN-26) followed by bottle top or cross-flow filtration with 0.2 μm pore size. 10 kDa Cross-flow filtration and buffer ex-changing (membrane made from regenerated cellulose was used with the following parameters: inlet pressure (P1) 4 bar, retentat pressure (P2) 1 bar, and the permeate was open to atmospheric pressure), was applied afterwards to concentrate, enrich, and purify the enzyme mix. The final enzyme solution was about 350 ml. For the enzyme mix first a qualitative enzyme activity pre-screen using colored carbohydrate polymers embedded in an agar matrix was proceeded. Extend of discoloration and the resulting diameter of the decolored halo around the applied enzyme solution is a measure of the present enzyme amount and relative activity correlated to the conversion of the substrates in this pre-screen test. Table 3 gives an overview of the substrates with the related enzyme activity.

TABLE 3

Overview of different substrates and respective enzyme activities.

| Substrate | Enzyme |
|---|---|
| Azo-CM-Cellulose | endo-1,4-β.Glucanase (Cellulase) |
| AZCL-HE-Cellulose | endo-1,4-β.Glucanase (Cellulase) |
| Azo-Alpha-Cellulase | endo-1,4-β.Glucanase (Cellulase) |
| Azo-Avicel | endo-1,4-β.Glucanase (Cellulase) |
| AZCL-Barley-β-Glucan | Malt-β-Glucanase (end-Cellulase) and Lichenase |
| AZCL-Xyloglucan | Endo-Cellulase |
| AZCL-Xylan | endo-1.4-β-Xylanase |
| AZCL-Arabinoxylan | endo-1.4-β-Xylanase |
| AZCL-Pachyman | endo-1,3-β-Glucanase (Cellulase) |
| AZCL-Dextran | endo-1,6-alpha-Dextranase |
| AZCL-Arabinan | endo-1,5-alpha-Arabinanase |
| Red-Arabinan | endo-1,5-alpha-Arabinanase |
| RedCL-Amylose | Alpha-Amylase |
| Red Starch | Alpha-Amylase |
| AZCL-Pullulan | Malt limit-dextrinase and Pullulanase |
| Red Pullulan | Malt limit-dextrinase and Pullulanase |
| Azo-Fructan | endo-Fructanase |
| AZCL-Chitosan | Chitosanase |
| Skim-milk platen | Protease |
| AZO-Casein | Protease |
| AZCL-Glalactan | endo-1,4-β-Galactanase |
| AZCL-Rhamnogalacturonan I | Rhamnogalacturonan hydrolase and lyase |
| AZCL-Galactomannan | endo-1,4-β-Mannanase |
| Olive oil Rhodamine B | lipase |

Enzyme activity was evaluated from no activity ("–"), activity ("+"), good activity ("++"), high activity ("+++"), very high activity ("++++") up to substrate mostly converted ("high"). Results of the enzyme screening are shown in Table 4.

TABLE 4

Results of the screening for enzymatic activity. The enzyme mix produced by *Aspergillus niger* comprises various enzymes, as shown below.

| | Substrate | Enzyme | Result |
|---|---|---|---|
| 1 | Azo-CM-Cellulose | endo-1,4-β.Glucanase (Cellulase) | +++ |
| 2 | AZCL-HE-Cellulose | endo-1,4-β.Glucanase (Cellulase) | ++++ |
| 3 | Azo-Alpha-Cellulase | endo-1,4-β.Glucanase (Cellulase) | – |
| 4 | Azo-Avicel | endo-1,4-β.Glucanase (Cellulase) | – |
| 5 | AZCL-Barley-β-Glucan | Malt-β-Glucanase (endo-Cellulase) and Lichenase | high |
| 6 | AZCL-Xyloglucan | Endo-Cellulase | high |
| 7 | AZCL-Xylan | endo-1.4-β-Xylanase | ++++ |
| 8 | AZCL-Arabinoxylan | endo-1.4-β-Xylanase | – |
| 9 | AZCL-Pachyman | endo-1,3-β-Glucanase (Cellulase) | – |
| 10 | AZCL-Dextran | endo-1,6-alpha-Dextranase | – |
| 11 | AZCL-Arabinan | endo-1,5-alpha-Arabinanase | – |
| 12 | Red-Arabinan | endo-1,5-alpha-Arabinanase | + |
| 13 | RedCL-Amylose | Alpha-Amylase | high |
| 14 | Red Starch | Alpha-Amylase | high |
| 15 | AZCL-Pullulan | Malt limit-dextrinase and Pullulanase | – |
| 16 | Red Pullulan | Malt limit-dextrinase and Pullulanase | ++ |
| 17 | Azo-Fructan | endo-Fructanase | – |
| 18 | AZCL-Chitosan | Chitosanase | – |
| 19 | Skim-milk platen | Protease | +++ |
| 20 | AZO-Casein | Protease | +++ |
| 21 | AZCL-Glalactan | endo-1,4-β-Galactanase | ++ |
| 22 | AZCL-Rhamnogalacturonan I | Rhamnogalacturonan hydrolase and lyase | – |
| 23 | AZCL-Galactomannan | endo-1,4-β-Mannanase | + |
| 24 | Olive oil Rhodamine B | lipase | – |

The enzyme screening showed high activity for the expected enzymes with bread residues as an inducing system. After this pre-screen, a targeted quantitative screen for the enzymes with high activity can be done subsequently.

The following method can be exemplified as the method for measuring the enzymatic activity of α-amylases. A α-amylase is allowed to act on endo-1,4-α-glucan bonds of soluble starch to generate dextrin and a mixture of reduced sugars (especially maltose). Dissolved 3,5-dinitrosalicylic acid (DNS) (by addition of 2M NaOH) is allowed to act on the generated reduced sugars in the presence of potassium-sodium tartrate-tetrahydrate at 95° C. to generate 3,5 amino nitro salicylic acid. Absorbance is measured at 540 nm, the amount of the 3-amino-5-nitrosalicylic acid is obtained by using a calibration curve and the enzymatic activity is calculated. The amount of the enzyme that liberates 1 μmol of reducing sugar out of soluble starch in 1 minute at 25° C. and pH 6.9 is defined as 1 U (1 unit).

The following method can be exemplified as the method for measuring the enzymatic activity of amyloglucosidase. A amyloglucosidase is allowed to act on 1,4-α-glucan bonds of maltose to generate D-glucose. Glucose oxidase is allowed to act on the generated glucose as a substrate in the presence of oxygen to generate hydrogen peroxide. Peroxidase is allowed to act on the generated hydrogen peroxide in the presence of aminoantipyrine and phenol to generate a quinoneimine dye. Absorbance is measured at 500 nm, the amount of the quinoneimine dye is obtained by using a calibration curve and the enzymatic activity is calculated. The amount of the enzyme that oxidises 1 μmol of maltose in 1 minute at 25° C. and pH 4.3 is defined as 1 U (1 unit).

The following method can be exemplified as the method for measuring the enzymatic activity of hemicellulase. A hemicellulase is allowed to act on xylose to generate reduced sugars. Dissolved 3,5-dinitrosalicylic acid (DNS) (by addition of 2M NaOH) is allowed to act on the generated reduced sugars in the presence of potassium-sodium tartrate-tetrahydrate at 95° C. to generate 3,5 amino nitro salicylic acid. Absorbance is measured at 540 nm, the amount of the 3-amino-5-nitrosalicylic acid is obtained by using a calibration curve and the enzymatic activity is calculated. The amount of the enzyme that liberates 1 μmol of reducing sugar out of xylose in 1 minute at 40° C. and pH 4.5 is defined as 1 U (1 unit).

The following method can be exemplified as the method for measuring the enzymatic activity of proteases. A protease is allowed to act on casein to generate amino acids. Reaction is stopped by adding trichloroacetic acid. The test solution is filtered by using a 0.45 μm polyethersulfone syringe filter subsequently and Folin & Ciolcaltea's, or Folin's Phenol reagent is allowed to act on the amino acids after filtration to generate a measurable color change that will be directly related to the activity of proteases. Absorbance is measured at 660 nm, the amount of the amino acid is obtained by using a tyrosine calibration curve and the enzymatic activity is calculated. The amount of the enzyme that produces amino acid equivalent to 10 μg tyrosin out of casein in 1 minute at 37° C. and pH 8.0 is defined as 1 U (1 unit).

The following method can be exemplified as the method for measuring the enzymatic activity of proteases. A protease is allowed to act on casein to generate amino acids. Reaction is stopped by adding trichloroacetic acid. The test solution is filtered by using a 0.45 μm polyethersulfone syringe filter subsequently and Folin & Ciolcaltea's, or Folin's Phenol Reagent is allowed to act on the amino acids after filtration to generate a measurable color change that will be directly related to the activity of proteases. Absorbance is measured at 660 nm, the amount of the amino acid is obtained by using a tyrosine calibration curve and the enzymatic activity is calculated. The amount of the enzyme that produces amino acid equivalent to 10 μg tyrosin out of casein in 1 minute at 37° C. and pH 8.0 is defined as 1 U (1 unit). As shown in table 4, an exemplary enzyme mix, i.e. an exemplary composition of the invention, comprises cellulose, lichenase, xylanase, arabinanase, amylase e.g. α-amylase, limit dextrinase, pullulanase, protease, galactanase, and mannanase.

Example 3: Production of Enzyme Solutions Via Cultivation of Fungi with Bread Residues as an Inducing System—*Ceratocystis*

In this experiment the present inventors studied the production of an enzyme solution via submerged fermentation with *Ceratocystis paradoxa* CBS 374.83 and bread residues as single media component. Therefore, cultivation and downstream processing was done as described in example 2. The final enzyme solution was about 30 ml. Results of the enzyme pre-screen proceeded as described in example 2 are shown in Table 5.

TABLE 5

Results of the screening for enzymatic activity. The enzyme mix produced by *Ceratocystis paradoxa* comprises various enzymes, as shown below.

| | Substrate | Enzyme | Result |
|---|---|---|---|
| 1 | Azo-CM-Cellulose | endo-1,4-β.Glucanase (Cellulase) | high |
| 2 | AZCL-HE-Cellulose | endo-1,4-β.Glucanase (Cellulase) | high |
| 3 | Azo-Alpha-Cellulase | endo-1,4-β.Glucanase (Cellulase) | – |
| 4 | Azo-Avicel | endo-1,4-β.Glucanase (Cellulase) | – |
| 5 | AZCL-Barley-β-Glucan | Malt-β-Glucanase (endo-Cellulase) and Lichenase | – |
| 6 | AZCL-Xyloglucan | Endo-Cellulase | – |
| 7 | AZCL-Xylan | endo-1.4-β-Xylanase | high |
| 8 | AZCL-Arabinoxylan | endo-1.4-β-Xylanase | high |
| 9 | AZCL-Pachyman | endo-1,3-β-Glucanase (Cellulase) | – |
| 10 | AZCL-Dextran | endo-1,6-alpha-Dextranase | – |
| 11 | AZCL-Arabinan | endo-1,5-alpha-Arabinanase | high |
| 12 | Red-Arabinan | endo-1,5-alpha-Arabinanase | high |
| 13 | RedCL-Amylose | Alpha-Amylase | high |
| 14 | Red Starch | Alpha-Amylase | high |
| 15 | AZCL-Pullulan | Malt limit-dextrinase and Pullulanase | – |
| 16 | Red Pullulan | Malt limit-dextrinase and Pullulanase | ++++ |
| 17 | Azo-Fructan | endo-Fructanase | – |

TABLE 5-continued

Results of the screening for enzymatic activity. The enzyme mix produced by *Ceratocystis paradoxa* comprises various enzymes, as shown below.

| Substrate | Enzyme | Result |
|---|---|---|
| 18 AZCL-Chitosan | Chitosanase | – |
| 19 Skim-milk platen | Protease | – |
| 20 AZO-Casein | Protease | – |
| 21 AZCL-Glalactan | endo-1,4-β-Galactanase | ++++ |
| 22 AZCL-Rhamnogalacturonan I | Rhamnogalacturonan hydrolase and lyase | ++++ |
| 23 AZCL-Galactomannan | endo-1,4-β-Mannanase | ++++ |
| 24 Olive oil Rhodamine B | lipase | – |

The enzyme screening showed high activity for the expected enzymes with bread residues as an inducing system. Examples of methods for a targeted quantitative screen of enzymes with high activity are given in example 2. As shown in table 5, an exemplary enzyme mix, i.e. an exemplary composition of the invention, comprises cellulase, xylanase, arabinanase, amylase e.g. α-amylase, limit dextrinase, pullulanase, galactanase, mannanase, rhamnogalacturonan hydrolase, and rhamnogalacturonan lyase.

Example 4: Hydrolysis of Food Residues—Bread

Saccharides, proteins and other nutrients contained in bread residues as described in example 1 are suitable for fermentation. Microorganisms convert it into profitable products such as microbial oil, useful product for food industry. Pretreating of substrate as bread residue can be applied before fermentation to get the nutrients easily accessible for microorganisms. One of typical pretreatment method is enzymatic hydrolysis. Bread residues contain high concentration of starch (more than 70% on dry matter) and proteins (up to 14% on dry matter) and treatment with α-amylases, glucoamylases and proteases easily lead to the release of compounds available for microbial growth. Hydrolysis of contained starch as main constituent of the bread dry weight comprise two stages. In the first stage α-amylase enzyme is used to liquefy the starch giving a solution including products of destrins and small amounts of glucose. The liquefied starch is subject to saccharification stage by using glucoamylase enzyme to obtain maximum terminal glucose conversion. Both stages have been found to be interrelated and there has been an optimal degree of liquefaction needed for adequate saccharification in the subsequent step. The following method is an exemplary enzymatic pretreatment of said substrates using one or more enzymes, for example a hydrolysis of starch, e.g. starch contained in bread residues. Homogenized bread residues in water suspension is prepared for the experiment. Size of bread particles are less than 4 mm. For liquefaction, α-amylase is added (e.g. SUG-001, Creative Enzymes, Shirley, NY; USA). Liquefaction is proceeded in a thermostat or water bath with specific pH (e.g. pH 6) and under specific temperature (e.g. 80° C.). The pH of the suspension is adjusted by e.g. 1% (w/v) solution of $H_2SO_4$ and 1% (w/v) solution of NaOH. The liquefaction is ended by freezing the suspension. Time of liquefaction is about 180 minutes. The saccharification is performed in liquefied suspension by addition of glucoamylase (e.g. SUG-002; DIS-1013, Creative Enzymes, Shirley, NY; USA). Saccharification is proceeded in a tempered shaker with specific pH (e.g. pH 4.2) and under specific temperature (e.g. 60° C.) and shaking (e.g. 130 rpm). Enzyme activity is ended by heating of the suspension at 80° C. for 5 minutes. Time of saccharification is at least 90 minutes. Hemicellulases (e.g. DIS-1023 Creative Enzymes, Shirley, NY; USA) and proteases (e.g. Neutrase, Novozymes, Denmark) are added in the saccharification step to yield the highest content of converted sugars and amino acids. Instead of using commercial available enzymes, enzyme mixes produced as described in example 2 and 3 or any combination of the foregoing are suitable. For example, the hydrolysis can be performed in only one step with elongated incubation time (e.g. 24 h) with specific pH (e.g. pH 5.5) specific temperature (e.g. 55° C.) and shaking (e.g. 130 rpm). An adaption of the procedure to a bioreactor is also possible.

After the incubation, the mixture is centrifugated (e.g. 14.000 rpm for 20 min) to separate not hydrolyzed solid residues and supernatant comprising the nutrients is collected. At this point the supernatant can be characterised as bread residue hydrolysate. This hydrolysate obtained from the protocol could be freeze-dried to assess the suitability of the nutrients to be rehydrated. For fermentation the hydrolysate could be freshly prepared or rehydrated applied as is or by optional addition of supplements singly or in mixture.

Example 5: Production of Microbial Food Ingredients—Microbial Lipids

Oleaginous microorganisms such as oleaginous yeasts represent interesting microbial lipid factories. Their rapid growth, along with the ability to utilize a wide variety of raw materials and their easy cultivation in large fermenters, make them highly suitable candidates for bio refinery processes. Oleaginous microorganisms such as oleaginous yeasts are able to grow and accumulate high levels of lipids. The strain ATCC 20509 *Cutaneotrichosporon oleaginosus* (*C. oleaginosus*) has been studied for its ability to accumulate TAGs by up to 70% of DCW, and advantageously has a fatty acid composition very similar to the fatty acid compositions of cocoa butter or palm oil. *C. oleaginosus* has the ability to use highly diverse carbon sources, e.g. carbon sources from food residue(s). The inventors have surprisingly found that food residue(s), such as bread residue, can be used as a substrate for obtaining nutrients for a growth medium for oleaginous microorganisms. For example, the inventors have successfully converted food residue(s) into nutrients using filamentous fungi and bacteria, and these nutrients can be used as growth medium for oleaginous microorganisms. Particularly, enzymatically treated food residue(s) can be used as nutrients, e.g. carbon source, for producing microbial lipids with oleaginous microorganisms e.g. *C. oleaginosus*. Hydrolysate obtained as described in example 4 is considered as a potential alternative carbon source for producing microbial lipids with *C. oleaginosus* fermentation.

Conventional lipid production with oleaginous organisms is a 2-step process, where the first step provides for biomass formation under non-limiting conditions (exponential growth phase), the second lipid induction step (nutrient limitation phase) affords high intracellular lipid accumulation at stagnant cell counts. It is also possible to do a *C. oleaginosus* co-fermentation with organic acid and carbon source leading to concurrently high biomass and lipid yields (84.9% of DCW) without the need of nutrient restriction that enables simultaneous assimilation of e.g. bread residue hydrolysate and acetic acid. A mild downstream processing is also favorable for producing edible microbial lipids. Therefore, performing e.g. a purely enzymatic treatment of *C. oleaginosus* without any solvent-based extraction or chemicals-based demulsification is suitable, to make the produced microbial lipids amenable for subsequent harvesting. Harvesting of the produced microbial lipids is done by a density-based separation method e.g. with a semi-continues centrifuge. Refining the microbial lipid is the last step of processing to get edible oil proceed e.g. physical refining. FIG. 1 shows a method that can be exemplified as a sustainable method for producing edible microbial lipids.

The following method can be exemplified as the method for analysing the fatty acid profile of the final product using gas chromatography with flame ionization detector (GC-FID) after methylation. The methylation is briefly done by incubating approx. 1 mg of oil with 1 ml of $NaOCH_3$ (for 20 minutes at 80° C.). Then 1 ml of HCl (37% in methanol) is added and the mixture is incubated again for 20 minutes at 80° C. Resulted fatty acid methyl esters (FAMEs) are extracted by hexane in injected GC-FID. The triglycerol C19:0 is used as an internal standard. An exemplary microbial lipid composition of *C. oleaginosus* is shown in Table 6.

TABLE 6

An exemplary microbial lipid composition produced using *C. oleaginosus*.

| Fatty Acid | Relative % |
|---|---|
| C14:0 (myristic acid) | 2.0 |
| C16:0 (palmitic acid) | 24.0 |
| C16:1 (palmitoleic acid) | 1.0 |
| C18:0 (stearic acid) | 10.0 |
| C18:1 (oleic acid) | 40.0 |
| C18:2 (linoleic acid) | 20.0 |
| C18:3 (linolenic acid) | 3.0 |

Example 6: Production of Microbial Food Ingredients—Microbial Proteins

The inventors have demonstrated that food residue(s), such as freeze-dried bread, can be used as a substrate to produce microbial protein biomass. Protein biomass is produced as a side product when cultivating the first microorganism.

Example 7: Production of Microbial Food Ingredients—Aroma Compounds

The inventors have surprisingly found that microorganisms, such as *Ceratocystis* species, produce aroma compounds when cultivated on food residue(s). For example, *Ceratocystis* species e.g. *Ceratocystis fimbriata* and *Ceratocystis moniliformis* produce a wide range of complex aroma such as: peach, banana, pear, rose or citrus depending on the strain and environmental conditions. The advantage of using these fungi consist of their relatively rapid growth and the variety of complex aroma mixtures synthesized. The inventors found that *Ceratocystis paradoxa* CBS 374.83 produced aroma compounds during the fermentation experiment as described in example 2 detected by a strong fruity smell of the supernatant. The supernatant comprised at least one aroma compound. Thus, the method of the invention surprisingly does not only provide microbial lipids, but also aroma compounds. To obtain the aroma compounds, a mild separation technique was used to provide an extract with sensory characteristics as close as possible to the complete product. For example, organophilic pervaporation (O-PV) which is a membrane-based technique was used for the mild recovery of natural aroma compounds, as well as solid-phase micro extraction (SPME) which is a non-exhaustive extraction technique in which a fiber coated with sorbent materials is exposed to the sample. The inventors have found that it is advantageous to maintain the ingredient functionality of the aroma during processing by using a mild separation technique.

The inventors further performed aroma fractionation to recover a particular aroma or a group of aroma compounds from a mixture of aroma compounds. Furthermore, the inventors analysed the extracted aroma compounds by capillary gas chromatography (GC) alone by comparing the retention indices of the sample with those of the corresponding authentic reference compound or via a GC-olfactometry (GC-O). GC-O enables the correlation between a volatile organic compound and its perception using the human nose as a detector. Therefore, the outlet of the GC capillary column is installed into a column flow splitter. The column flow splitter possesses two outlets directing the gas flow into a destructive detector e.g. flame ionization detector (FID) or a mass spectrometer (MS) and into a nondestructive olfactory detection part (ODP). With this equipment it is possible to directly assign an odor impression to a MS spectrum or FID peak.

Example 8: Usage of Microbial Components in Food Industry—Microbial Lipids in Bakery Products A broad spectrum of applications to microbial components in food industry is possible. The inventors exemplary used the microbial lipids obtained with a method of the invention in different bakery products:

a) Kaiser roll

Ingredients:

- 100% flour type 550 or 650
- 2-3% buttermilk
- 3-4% baker's yeast
- 10-15% microbial lipid
- 2-3% baking agent
- 1.8-2.2% salt
- 55-63% water Kneading:

- Starter dough
  - Mixing of 20% flour, 2% buttermilk, 10% water and 1% baker's yeast to get a smooth dough using a dough kneader at lowest level 3 to 4 minutes followed by 2 to 3 minutes of rapid mixing. Covering the starter dough subsequently with cling film and rest it in a fridge (4° C.) for 6 to 24 hours.
- Main dough
  - Slowly kneading of 80% flour, 3% baking agent, 2% salt, 15% microbial lipid, 3% baker's yeast and starter dough thoroughly with a spiral kneader 5 to 7 minutes followed by 5 to 8 minutes fast kneading till the dough is mouldable.

The dough temperature ranges between 23 and 26° C.

After removing the dough out of the spiral kneader the dough sits for up to 10 minutes.

Processing:

Portions of 1800 to 2100 g are rounded and covered with cling film subsequently.

Let it rest for 15 to 20 minutes so that the dough can rise briefly.

Moulding of the portions followed by rounding.

Put it on a food carrier and let it rise in a proofing chamber (Temperature 30-35° C. with a relative humidity of 75-85%) for 50 to 75 minutes.

Baking:

Oven temperature: 230-240° C.

Steam input: standard

Damper: closed

Baking time: approx. 20 minutes

Kaiser rolls were successfully produced with microbial lipids produced with a method of the invention. The bread rolls produced using microbial lipid had the same smell, taste, and texture as conventional Kaiser rolls.

b) Pretzel

Ingredients:

100% wheat flour type 550

2-3% bakery malt 1.8-2.2% salt 10-15% microbial lipid 1.5-2% baker's yeast 45-48% water Kneading:

Starter dough

Mixing of 20% flour, 0.2% baker's yeast and 12% water (10° C.) using a dough kneader at lowest level 3 to 4 minutes followed by 3 minutes of rapid mixing at highest level. Covering the starter dough subsequently with cling film and rest it at room temperature for 1 hour. Then leave it for rising for 12 to 14 hours.

Main dough

Slowly kneading of 80% flour, 2% bakery malt, 2% salt, 1.5% baker's yeast, 10% microbial lipid, 10% water (10° C.) and starter dough with a spiral kneader 4 minutes at low level followed by 5 minutes fast kneading hat highest level.

The dough temperature is approx. 24° C.

After removing the dough out of the spiral kneader the covered dough sits for approx. 20 minutes.

Processing:

Portions of 1800 to 2100 g are rounded and covered with cling film subsequently.

Let it rest for 15-20 minutes.

Moulding of the portions.

Roll dough in portions on a floured work surface to strands with a length of approx. 60 cm so that the largest diameter of the strands is in the center and the strands become narrower towards the outside with rounded tips.

Twisting every straight rope of dough to form it into pretzel shape.

Put the dough pieces on a baking tray covered with baking linen.

Covering of portions with cling film subsequently and let it rest for 1 to 2 hours at room temperature so that the dough has risen to double volume.

Provide the pretzel lye and put on eye protection and protective gloves.

Submerge the pretzels in lye for approx. 5 seconds, remove them and put them on a baking tray covered with baking paper.

Cut the pretzels at the bulbous part and sprinkle them with some salt.

Baking:

Oven temperature: preheated 230° C. top and bottom heat

Baking time: 12 to 14 minutes till gold brown

Pretzels are cooled on a wire rack subsequently.

Pretzels were successfully produced with microbial lipids produced with a method of the invention. The Pretzels produced using microbial lipid had the same smell, taste, and texture as conventionally produced Pretzels.

c) Bismarck

Ingredients:

100% flour type 550 or 405

20-30% milk 5-8% baker's yeast

20% eggs

8% egg yolk 10-15% microbial lipid

10% sugar 1.8-2.2% salt 60 g water

Aroma: vanilla and lemon zest

Kneading:

Starter dough

Mixing of 30% flour, 20% milk, 5% baker's yeast and 60 g water (10° C.) to get a smooth dough using a dough kneader at lowest level 3 to 4 minutes. Covering the starter dough subsequently with cling film and rest it at room temperature for 30 minutes.

Main dough

Slowly kneading of 70% flour, 20% eggs, 8% egg yolk, 10% microbial lipid, 10% sugar, 7% milk, 2% salt, aroma and starter dough thoroughly with a spiral kneader 5 to 7 minutes followed by 10 to 12 minutes fast kneading till the dough is mouldable.

After removing the dough out of the spiral kneader the dough sits between 20 and 30 minutes.

Processing:

Portions of 1200 to 1500 g are rounded and covered with cling film subsequently.

Let it rest for 15 to 20 minutes so that the dough can rise briefly.

Moulding of the portions followed by rounding.

Put it on a food carrier and let it rise in a proofing chamber (Temperature 30-35° C. with a relative humidity of 60-70%) for 50 to 75 minutes.

Stiffening:

The proofing of the dough pieces is interrupted so that the surface gets completely dry and solid.

Boiling:

Fill in microbial lipid in a chip pan and heat it up to 150-175° C.

Check temperature.

Bake on the dough pieces with the round part upwards.

Turn them afterwards and press them down with a grid towards the end of baking time.

Baking time: 6 to 8 minutes with optimum intervals of 3 min./2 min./30 seconds and 30 seconds.

Filling:

Filling like apricot jam is placed in the center of the bismarcks.

Topping:

Still hot bismarcks are dusted with e.g. sugar or icing sugar.

Bismarcks (German doughnut with no central hole) were successfully produced with microbial lipids produced with a method of the invention. The bismarcks produced using microbial lipid had the same smell, taste, and texture as conventionally produced bismarcks.

d) Fruit loaf

Ingredients:

30% wheat flour type 550
20-30% milk
1.5% baker's yeast
8.5% water
13% microbial lipid
3% sugar
2% marzipan
1.8-2.2% salt
0.3% sour cream
0.3% spice
1% milk powder
0.3% rum aroma
0.3% vanilla aroma
0.3% almonds bitterly
0.3% lemon zest
19% sultanas
0.4% almonds baton-cut
0.4% candied orange and lemon peel
4.5% Overseas rum Kneading:

Starter dough

Mixing of 10% wheat flour, 1.5% baker's yeast, 7% water and 0.3% salt with a dough kneader at lowest level for 2 minutes followed by 3 to 4 minutes fast kneading to get a cool (dough temperature is 24° C.) and semisolid starter dough. Covering the starter dough subsequently with cling film and rest it at room temperature for 30 minutes. After removing the dough out of the spiral kneader rest it in a fridge (5° C.) for 10 to 15 hours.

Main dough

Mixing of all other ingredients of the main dough except flour to get a smooth dough. Add starter dough and flour subsequently and mix it slowly for 5 minutes followed by 3 minutes fast kneading. After a briefly dough relaxation the fruit loaf mixture is filled.

Processing:

Weight portions are rounded 15 minutes dough relaxation and elongation subsequently.

Cover it and do the proofing at room temperature.

Moulding of the portions followed by rounding.

Put it on a food carrier and let it rise in a proofing chamber (Temperature 30-35° C. with a relative humidity of 60-70%) for 50 to 75 minutes.

Baking:

Oven temperature: start 210° C. decreasing to 200° C.

Steam input: none

Damper: opened after 5 minutes baking time

Baking time: approx. 50 minutes for 780 g dough pieces

Still hot coat it with liquid butter and turn it in vanilla sugar subsequently.

After cooling the fruit loaf is dusted with "sweet snow".

Fruit loaf was successfully produced with microbial lipids produced with a method of the invention. The fruit loaf produced using microbial lipid had the same smell, taste, and texture as conventionally produced fruit loaf.

Example 9: Use of Microbial Components in Food Industry—Chocolate Products

It is possible to produce numerous food products using microbial lipids produced with a method of the invention. For example, the following products can be produced:

| Chocolate spread | |
|---|---|
| Sugar | 10-70% |
| Microbial lipids | 5-60, |
| Plant lipids (eg. palm oil and/or cocoa butter): | 0-20 |
| hazelnuts | (0-20%), |
| skim milk powder | (0-10%) |
| whey powder | (0-10%) |
| cocoa (including cocoa products or any product that is cocoa alternative that have cocoa taste-and smell-like | (5-25%), |
| Additions (Including: non-fat milk solids, emulsifier (lecithin INS 322), flavour (vanillin) contains added flavour (nature identical flavouring substance - vanillin). | 1-5% |

| Chocolate bar | |
|---|---|
| Sugar, | 10-70% |
| Microbial lipids | 10-50, |
| Plant lipids (eg. palm oils and/or cocoa butter): | 0-40 |
| Skimmed milk powder: | 0-15% |
| Cocoa: | 20-70%. |
| Additions (Including: hazelnuts non-fat milk solids, other nuts and wheat, whey powder, soy components emulsifier (lecithin INS 322), flavour (vanillin) contains added flavour (nature identical flavouring substance - vanillin). | 1-10% |

| Dark Chocolate bar | |
|---|---|
| Sugar, | 1-20% |
| Microbial lipids | 10-50, |
| Plant lipids (eg. palm oils and/or cocoa butter): | 0-40 |
| Skimmed milk powder: | 0-15% |
| Cocoa: | 50-80%. |
| Additions (Including: hazelnuts non-fat milk solids, other nuts and wheat, whey powder, soy components emulsifier (lecithin INS 322), flavour (vanillin) contains added flavour (nature identical flavouring substance - vanillin). | 1-10% |

| MARGARINE | |
|---|---|
| Microbial Lipids | 1-80% |
| Plant Lipids (Palm oil, rapeseed oil, Sunflower oil and/or olive oil) | 0-50% |
| Salt: | 1-5% |
| Water: | 10-30% |
| Additions [Such as emulsifier (eg. E475; E471; lecithins); acid (e.g. citric acid); natural flavour; colour (carotenes)] | 1-3% |

Example 10: Changing the Triglycerides Content Over Modeling the Process Parameters Changing the triglycerides content over modeling the process parameters. TAG composition of Yeast oil (%)

| | Yeast Oil 1 | Yeast Oil 2 | Yeast Oil 3 | Yeast Oil 4 |
|---|---|---|---|---|
| Unknown | 0.5 | 1.7 | 1.7 | 9.4 |
| Other Liquid TAGs | 8.7 | 8.1 | 9.0 | 22.3 |
| PLiP | 2.6 | 0.8 | 0.7 | 8.4 |
| MOP/PPoP | 1.1 | 0.2 | 0.2 | 1.3 |
| OOO | 3.5 | 6.6 | 7.6 | 5.9 |
| POO | 17.0 | 13.9 | 15.6 | 32.9 |
| PLiS | 2.5 | 1.8 | 1.7 | 1.4 |
| POP | 19.5 | 26.6 | 25.9 | 11.6 |
| PPP | 0.2 | 0 | 0 | 0.0 |
| SOO | 7.1 | 13.2 | 14.4 | 4.0 |
| SLiS | 0.4 | 0.2 | 0.2 | 0.2 |
| POS | 21.2 | 5.1 | 4.8 | 1.6 |
| SOS | 4.2 | 11.1 | 8.8 | 0.2 |
| SSS | 0.5 | 0.9 | 0.8 | 0 |
| PSS | 0 | 0.1 | 0.1 | 0 |
| Other high melting TAGs | 1.6 | 1.2 | 0.3 | 0.0 |

P; palmitic,
St; stearic,
O; oleic,
Li; linoleic,

REFERENCES

[1] Lieken. (2021 Apr. 12). Lieken Brot-und Backwaren GmbH. Retrieved from www.lieken-urkorn.de: https://www.lieken-urkorn.de/produkte/produkt/bauernmild-500g

[2] USDA1. (2021 Apr. 12). USDA, Agricultural Research Service, Fooddata central. Retrieved from https://fdc.nal.usda.gov/fdc-app.html #/food-details/172686/nutrients

[3] USDA2. (2021 Apr. 12). USDA, Agricultural Research Service, Fooddata central. Retrieved from https://fdc.nal.usda.gov/fdc-app.html #/food-details/172684/nutrients The features of the present invention disclosed in the specification, the claims, and/or in the accompanying figures may, both separately and in any combination thereof, be material for realizing the invention in various forms thereof.

The invention claimed is:

1. A method for producing microbial lipids, said method comprising the steps:

a) providing a first substrate, wherein said first substrate is a food residue(s);

b) cultivating a first microorganism selected from filamentous fungi and bacteria with said first substrate, and thereby allowing said first microorganism to produce at least one enzyme and an enzymatically treated first substrate;

c) optionally, obtaining said at least one enzyme and pretreating a second substrate with said at least one enzyme, and thereby providing an enzymatically treated second substrate; wherein said second substrate is a food residue(s);

d) cultivating a second microorganism, wherein said second microorganism is an oleaginous microorganism, with a medium comprising said enzymatically treated first substrate and/or, if the step c) is present, with a medium comprising said enzymatically treated second substrate, and thereby allowing said oleaginous microorganism to produce microbial lipids;

e) performing a purely enzymatic treatment of said cultivated second microorganism without any solvent-based extraction or chemicals-based demulsification, to make said microbial lipids produced in the step d) amenable for subsequent harvesting; and f) harvesting said microbial lipids produced in the step d).

2. The method according to claim 1, wherein said food residue(s), at each occurrence, is independently selected from food residue(s) comprising bakery food residue(s); fruit food residue(s); vegetable food residue(s); bran or bran flour; fish food residue(s); sea food residue(s); brewer's spent grain; cereal food residue(s); restaurant leftovers; animal product food residue(s); food with expired expiration date; and any combination thereof.

3. The method according to claim 1, wherein said filamentous fungi are selected from *Ceratocystis* sp.; *Trichoderma* sp.; *Aspergillus* sp.; *Neurospora* sp.; *Monascus* sp.; *Rhizopus* sp.; *Fusarium* sp.; *Thermomyces* sp; *Aureobasillium* sp.; *Ischnoderma* sp.; *Polyporus* sp.; *Pycnoporus* sp.; *Phanerochaete* sp.; and *Xylaria* sp; and/or wherein said bacteria are selected from *Clostridium* sp.; *Halobacillus* sp.; *Halomonas* sp.; *Rhodothermus* sp.; *Streptomyces* sp.; and *Bacillus* sp.

4. The method according to claim 1, wherein the oleaginous microorganism is selected from oleaginous yeasts, oleaginous fungi, oleaginous bacteria, and oleaginous microalgae;

wherein said oleaginous yeasts are selected from *Cutaneotrichosporon* sp.; *Trichosporon* sp.; *Rhodospirillum* sp.; *Rhodosporidium* sp.; *Rhodosporon* sp.; *Candida* sp.; *Cryptococcus* sp.; *Lipomyces* sp.; *Yarrowia* sp.; *Rhodotorula* sp.; and *Apiotrichum* sp.;

said oleaginous fungi are selected from *Cunninghamella* sp.; *Aspergillus* sp.; *Neurospora* sp.; *Monascus* sp.; *Rhizopus* sp.; *Fusarium* sp.; *Mucor* sp.; *Mortierella* sp.;

said oleaginous bacteria are selected from *Rhodococcus* sp.; *Acinetobacter* sp.; and *Bacillus* sp.; and said oleaginous microalgae are selected from *Chlorella* sp., *Pseudochlorococcum* sp., *Nannochloris*sp., *Nannochloropsis* sp., *Isochrysis* sp., *Tribonema* sp., *Dunaliella* sp., *Ankistrodesmus* sp., *Botryococcus* sp., *Pavlova* sp., *Scenedesmus* sp., *Skeletonema* sp., and *Nitzschia* sp.

5. The method according to claim 1, wherein said second microorganism is an oleaginous yeast selected from *Cutaneotrichosporon oleaginosus, Trichosporon oleaginosus, Trichosporon capitatu, Trichosporon asahii, Lipomyces starkeyi, Rhodosporidium toruloides, Yarrowia lipolytica, Rhodotorula graminis, Rhodotorula gracilis, Rhodotorula glutinis, Apiotrichum curvarum, Cryptococcus curvatus, Candida viswanathii*, and *Candida freyschussii.*

6. The method according to claim 1, wherein said step b) of said method comprises cultivating the first microorganism selected from the filamentous fungi and the bacteria with said first substrate, and thereby allowing said first microorganism to produce at least one enzyme, an enzymatically treated first substrate, and protein biomass and/or aroma compounds.

7. The method according to claim 6, wherein said method further comprises a step of harvesting said protein biomass and/or said aroma compounds.

8. The method according to claim 1, wherein said medium further comprises an additional carbon source, nitrogen source, trace metal, and/or vitamin.

9. The method according to claim 1, wherein said method further comprises a step of pretreating said first substrate and/or, if the step c) is present, pretreating said second substrate, by mechanical pretreatment;

dissolving said substrate(s) in a dissolvent;

chemical hydrolysis of said substrate(s);

thermal pretreatment of said substrate(s);

fermentative pretreatment of said substrate(s); and/or enzymatic pretreatment of said substrate(s) using one or more enzymes;

wherein said one or more enzymes are selected from proteases; and hydrolases.

10. The method according to claim 1, wherein said method comprises said step e) of performing said purely enzymatic treatment of said cultivated second microorganism without any solvent-based extraction or chemicals-based demulsification, wherein said purely enzymatic treatment of said cultivated second microorganism is a treatment of said microorganism with a hydrolase, alone, or in combination with/followed by a protease.

11. The method according to claim 1, wherein said method comprises the step c) of obtaining said at least one enzyme and pretreating said second substrate with said at least one enzyme, wherein said pretreating comprises contacting said second substrate with said at least one enzyme in the form of a liquid enzyme preparation obtained from culturing said first microorganism, or in the form of a freeze-dried enzyme preparation.

12. The method according to claim 1, wherein said at least one enzyme contains one or more activities selected from enzyme activities of cellulase; lichenase; xylanase;

arabinanase; amylase; pullulanase; protease; galactanase; mannanase; rhamnogalacturonan hydrolase; rhamnogalacturonan lyase; xyloglucanase; hemicellulase; amyloglucosidase; beta- glucosidase; pectinase; and laminarinase.

13. The method according to claim 1, wherein said method is a method of producing microbial lipids and preparing foodstuff therefrom, wherein said method further comprises a step g) of preparing a foodstuff comprising the microbial lipid harvested in the step f).

14. A method for the production of a foodstuff wherein said method comprises use of a microbial lipid produced using a method according to claim 1.

15. The method according to claim 2, wherein the food residue is the bread food residue.

16. The method according to claim 4, wherein said second microorganism is the oleaginous yeast selected from *Cutaneotrichosporon* sp.

17. The method according to claim 1, wherein the step b) comprises co-cultivating one or more microalgae with said first microorganism, and thereby allowing said one or more microalgae to produce protein biomass, microbial lipids, and/or aroma compounds.

18. The method according to claim 17, wherein the one or more microalgae are selected from *Chlorella* sp.; *Scenedesmus* sp.; *Dunaliella* sp.; *Haematococcus* sp.; *Crypthecodinium* sp.; *Schizochytrium* sp.; and *Tetraselmis* sp.

19. A food-grade composition comprising at least five enzymes selected from cellulase; lichenase; xylanase; arabinanase; amylase, e.g., a-amylase; limit dextrinase; pullulanase;

protease; galactanase; mannanase; rhamnogalacturonan hydrolase; rhamnogalacturonan lyase;

xyloglucanase; amyloglucosidase; beta-glucosidase; pectinase; and laminarinase; wherein one of the at least five enzymes is limit dextrinase.

* * * * *